United States Patent [19]
Sawyer et al.

[11] Patent Number: 5,149,880
[45] Date of Patent: Sep. 22, 1992

[54] NITROGEN-CONTAINING AROMATIC HETEROCYCLIC LIGAND-METAL COMPLEXES AND THEIR USE FOR THE ACTIVATION OF HYDROGEN PEROXIDE AND DIOXYGEN IN THE REACTION OF ORGANIC COMPOUNDS

[75] Inventors: Donald T. Sawyer; Ceshing Sheu; Andrzej Sobkowiak; Hui-Chan Tung, all of College Station, Tex.

[73] Assignee: The Texas A & M University System, College Station, Tex.

[21] Appl. No.: 573,346

[22] Filed: Aug. 24, 1990

Related U.S. Application Data

[63] Continuation-in-part of Ser. No. 466,485, Jan. 16, 1990, abandoned.

[51] Int. Cl.$^5$ .............................................. C07C 45/28
[52] U.S. Cl. .................................. 568/342; 568/311; 568/385; 568/815; 568/818; 568/822; 568/910; 568/320; 568/360; 568/399; 568/401; 568/431; 568/400
[58] Field of Search ............... 568/330, 385, 311, 342, 568/320, 360, 399, 400, 401, 431

[56] References Cited

U.S. PATENT DOCUMENTS

| | | | |
|---|---|---|---|
| 4,028,423 | 6/1977 | Brawnstein et al. | 568/360 |
| 4,259,527 | 3/1981 | Maus et al. | 568/342 |
| 4,341,907 | 7/1982 | Zelonka | 568/360 |
| 4,482,746 | 11/1984 | Humolin | 568/342 |
| 4,659,829 | 4/1987 | Saussine et al. | 568/342 |
| 4,978,799 | 12/1990 | Sanderson et al. | 568/385 |

FOREIGN PATENT DOCUMENTS 0266283 5/1988 European Pat. Off. ............ 568/360

Primary Examiner—James H. Reamer
Attorney, Agent, or Firm—Curtis, Morris & Safford

[57] ABSTRACT

Nitrogen-containing aromatic heterocyclic ligand-metal complexes and their use for the activation of hydrogen peroxide and dioxgen are disclosed. Processes whereby activated hydrogen peroxide or dioxygen are used to transform various organic substrates are also disclosed. In particular, processes for the conversion of methylenic carbons to carbonyls, for the dioxygenation of aryl olefins, acetylenes and aryl-α-diols, for the oxidation of alcohols and aldehydes and for the removal of mercaptans from gaseous streams and for the removal of hydrogen sulfide and/or mercaptans from liquid streams are disclosed.

6 Claims, No Drawings

NITROGEN-CONTAINING AROMATIC HETEROCYCLIC LIGAND-METAL COMPLEXES AND THEIR USE FOR THE ACTIVATION OF HYDROGEN PEROXIDE AND DIOXYGEN IN THE REACTION OF ORGANIC COMPOUNDS

This invention was made with government and private support, including the National Science Foundation under Grant CHE-8516247, a Graduate Fellowship by the Welch Foundation under Grant A-1042, and a Fellowship from the U.S. Air Force Institute of Technology Civilian Institute Program.

This application is a continuation-in-part of application Ser. No. 07/466,485, filed Jan. 16, 1990, the disclosure of which is incorporated herein by reference.

FIELD OF THE INVENTION

This invention pertains generally to organic ligand-metal complexes and their use in chemical reactions and more particularly to nitrogen-containing aromatic heterocyclic ligand-transition metal complexes and their use for the activation of dioxygen and/or hydrogen peroxide for the ketonization of methylenic carbons, and the dioxygenation of acetylenes, olefins and α-aryl-diols, and for the removal of mercaptans from gaseous streams and for the removal of hydrogen sulfide and/or mercaptans from liquid streams.

Several publications are referenced in this application by Arabic numerals within parentheses. Full citations for these references are found at the end of the specification immediately preceding the claims. The disclosures of these publications are incorporated by reference into this application in order to more fully describe the state of the art to which this invention pertains.

BACKGROUND OF THE INVENTION

The conversion of methylenic carbons to ketones, e.g., the conversion of cyclohexane to cyclohexanone, is important in the manufacture of useful synthetic materials. Indeed, cyclohexanone is the principal starting material in the synthesis of adipic acid which in turn is used to make nylon and dacron. In addition, the ability to dioxygenate organic substrates would afford numerous alternatives in the total synthesis of pharmaceuticals and biomolecules, e.g., antibiotics, steroids, hormones and the like. Thus, the utility and desirability of efficient and inexpensive methods for the conversion of methylenic carbons to ketones and for the dioxygenation of organic substrates are manifest.

Several reports (1-5) have described the selective transformation of methylenic groups ($>CH_2$) to ketones via four heterogeneous iron-dioxygen systems; (a) iron powder/sodium sulfide/$O_2$, (b) $Fe_3O(OAc)_6.3.5$ pyridine(py)/zinc dust/$O_2$, (c) $(py)_4FeCl_2/KO_2(s)$, and (d) $(py)_4FeCl_2/(O_2+e^-\rightarrow O_2^-.)$ in 4:1 pyridine/acetic acid. These systems are postulated to contain σ-bonded iron-carbon intermediates (6) with superoxide ion ($O_2^-\cdot$) as the active form of reduced oxygen, which oxidizes the iron catalyst within the catalytic cycle. Pyridine is believed to be essential to the system as a trap for hydroxyl radical, thereby preventing Fenton chemistry. Acetic acid serves as a proton source to transform superoxide ion to hydroperoxyl radical ($HOO\cdot$). However, these heterogeneous iron-dioxygen systems proved to be inefficient and resulted in the indirect production of hydrogen peroxide from superoxide ion.

Other experiments with other iron complexes, or other solvent matrices, are reported to yield a spectrum of products that are characteristic of Fenton chemistry ($\cdot OH$) (4). In addition, it has been reported (7) that $[Fe(MeCN)_4](ClO_4)_2$ in anhydrous acetonitrile activates excess HOOH for the dioxygenation of diphenylisobenzofuran, rubrene, acetylenes, cis-stilbene, and methylstyrene. However, the system is essentially unreactive with saturated hydrocarbons, and the presence of basic ligands ($H_2O$ or pyridine) causes the system to promote Fenton chemistry [Fe(II)+HOOH→Fe$^{III}$OH+$\cdot$OH] (8).

OBJECTS, FEATURES AND ADVANTAGES OF THE INVENTION

It is therefore a general object of the invention to overcome the disadvantages described above by providing herein an efficient process for the activation of hydrogen peroxide or dioxygen.

It is another object of the invention to provide a process for the dioxygenation of an organic compound by activation of hydrogen peroxide or dioxygen.

It is a further object of the invention to provide a process for the ketonization of methylenic carbons in organic compounds, the oxidation of alcohols and aldehydes and the dioxygenation of acetylenes, olefins, arylolefins, acetylenes and aryl-α-diols by the activation of hydrogen peroxide.

It is another object of the invention to provide a process for the ketonization of methylenic carbons in organic compounds and the dioxygenation of acetylenes, olefins and aryl-α-diols by activation of dioxygen.

It is another object of the invention to provide a process for the removal of mercaptans from gaseous streams.

It is another object of the invention to provide a process for the removal of hydrogen sulfide and/or mercaptans from liquid streams.

It is yet another object of the invention to provide novel aromatic heterocyclic ligand-metal complexes for the activation of hydrogen peroxide and dioxygen.

These and other objects, features and advantages of the invention will become apparent from the following description of the invention.

SUMMARY OF THE INVENTION

The invention is broadly directed to a process for the activation of hydrogen peroxide or dioxygen which comprises contacting dioxygen or hydrogen peroxide with a complex of formula

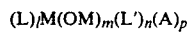

wherein:
L and L' are the same or different and each is a 5 to 10 member aromatic heterocyclic ligand containing at least one nitrogen atom which heterocyclic ligand is unsubstituted or mono- or polysubstituted by $CO_2^-$, $CO_2H$, $O^-$, OH, alkyl, cycloalkyl or aryl which in turn is unsubstituted or mono- or polysubstituted by $CO_2^-$, $CO_2H$, $O^-$, OH, alkyl or cycloalkyl;
M is a transition metal cation;
A is an anion;
l is 1, 2, 3 or 4;
m is 0 or 1;
n is 0, 1, 2, 3 or 4; and p is 0, 1, 2 or 3; under conditions suitable for the activation to take place, provided that if dioxygen is to be activated, L is at least monosubstituted by $CO_2^-$ or $CO_2H$ when M is Fe. In particular, L and L' are the same or different and each is a ligand of formula

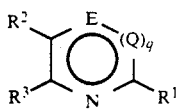

wherein:
$R^1$ is hydrogen, $CO_2^-$ or $CO_2H$;
$R^2$ is hydrogen or alkyl;
$R^3$ is hydrogen, $CO_2^-$, $CO_2H$ or pyridinyl; or
$R^2$ and $R^3$ joined together and taken with the other atoms in the ring form a quinoline ring which is unsubstituted or substituted in the 8-position by $O^-$;
E is CH, N, NH or $CR^4$ wherein $R^4$ is alkyl;
Q is CH;
q is 0 or 1 provided that when q is 0, there is no Q substituent, E and the carbon atom to which $R^1$ is attached are joined directly and E is NH;
M is a transition metal cation;
A is anion of an organic or mineral acid or is a halogen anion;
l is 1, 2, 3 or 4;
m is 0 or 1;
n is 0, 1, 2, 3 or 4; and
p is 0, 1 or 2; under conditions suitable for the activation to take place, provided that when dioxygen is to be activated, M in the complex is in its reduced state and $R^1$ and $R^3$ are the same or different and each is $CO_2^-$ or $CO_2H$ when M is Fe.

The invention is also directed to a process for the dioxygenation of an organic compound which comprises contacting the organic compound with a complex of the formula described above in the presence of hydrogen peroxide or dioxygen under conditions suitable for the dioxygenation to take place, provided that if the contact is made in the presence of dioxygen, then M in the complex is in its reduced state and L is at least monosubstituted by $CO_2^-$ or $CO_2H$ when M is Fe.

In another aspect, the invention is directed to a process for the oxygenation of an organic compound which comprises contacting the organic compound with a complex of the formula described above in the presence of hydrogen peroxide or dioxygen under conditions suitable for the oxygenation to take place, provided that if contact is made in the presence of dioxygen, then M in the complex is in its reduced state and L is at least monosubstituted by $CO_2^-$ or $CO_2H$ when M is Fe. In one embodiment, a methylenic carbon contained in an organic compound, in particular a hydrocarbon, is converted to a ketone. In another embodiment, an aromatic hydrocarbon is converted to an alcohol.

The invention is also directed to a process for the conversion of an acetylene to an α-dicarbonyl which comprises contacting the acetylene with a complex of the formula described above in the presence of hydrogen peroxide or dioxygen under conditions suitable for the conversion to take place, provided that if contact is made in the presence of dioxygen, then M in the complex is in its reduced state and L is at least monosubstituted by $CO_2^-$ or $CO_2H$ when M is Fe.

In still another aspect, the invention is directed to a process for the conversion of an olefin to an aldehyde and/or a ketone which comprises contacting the olefin with a complex of the formula described above in the presence of hydrogen peroxide or dioxygen under conditions suitable for the conversion to take place, provided that if the contact is made in the presence of dioxygen, then M in the complex is in its reduced state and L is at least monosubstituted by $CO_2^-$ or $CO_2H$ when M is Fe.

In another specific embodiment, the invention is directed to a process for the conversion of an aryl-α-diol to a carboxylic acid, a dicarboxylic acid or dicarboxylic acid anhydride which comprises contacting the aryl-α-diol with a complex of the formula described above in the presence of hydrogen peroxide or dioxygen under conditions suitable for the conversion to take place, provided that if the contact is in the presence of dioxygen, then M in the complex is in its reduced state and L is at least monosubstituted by $CO_2^-$ or $CO_2H$ when M is Fe.

Another embodiment of the invention is directed to a process for the oxidation of an alcohol or aldehyde which comprises contacting an alcohol or an aldehyde with a complex of the formula described above in the presence of hydrogen peroxide or dioxygen under conditions suitable for the oxidation to take place, provided that if the contact is made in the presence of dioxygen, M is in its reduced state and L is at least monosubstituted by $CO_2^-$ or $CO_2H$ when M is Fe.

In still another embodiment, the invention is directed to a process for removing a mercaptan from gas streams or for removing hydrogen sulfide or a mercaptan from liquid streams which comprises contacting a gas stream containing a mercaptan or a liquid stream containing hydrogen sulfide or a mercaptan with a complex of the formula as described above in the presence of dioxygen under conditions suitable for the conversion of the hydrogen sulfide or the mercaptan to elemental sulfur, provided M in the complex is in its reduced state and L is at least monosubstituted by $CO_2^-$ or $CO_2H$ when M is Fe.

In another aspect, the invention is directed to novel complexes of formula

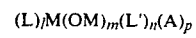

wherein:
L and L' are the same or different and each is a ligand of formula

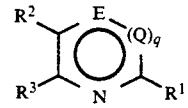

wherein
$R^1$ is hydrogen, $CO_2^-$ or $CO_2H$;
$R^2$ is hydrogen;
$R^3$ is hydrogen, $CO_2^-$, $CO_2H$ or pyridinyl; or
$R^2$ and $R^3$ joined together and taken with the other atoms in the ring form a quinoline ring which is unsubstituted or substituted in the 8-position by $O^-$;
E is CH, N, NH or $CR^4$ wherein $R^4$ is alkyl;
Q is CH;

q is 0 or 1 provided that when q is 0, there is no Q substituent, E and the carbon atom to which $R^1$ is attached are joined directly and E is NH;

M is a transition metal cation;

A is an anion of an organic or mineral acid or is a halogen anion;

l is 1, 2, 3 or 4;

m is 0 or 1;

n is 0, 1, 2, 3 or 4; and p is 0, 1 or 2; excluding complexes wherein:

L is pyridine, M is Cu or Mn, A is $Cl^-$, $Br^-$, $I^-$, $Cl^-$, $ClO_4^-$ or $NO_3^-$, l is 2, m=n=0 and p is 1;

L is pyridine, M is Fe, A is $Cl^-$, l is 4, m=n=0 and p is 2;

L is 2,2'-bipyridine, M is Cu or Mn, A is $Cl^-$, $Br^-$, $I^-$, $Cl^-$, $ClO_4^-$ or $NO_3^-$, l is 1, m=n=0 and p is 1;

L is 2,2'-bipyridine, M is Ru, l is 3 and m=n=p=0;

L is picolinate, M is Fe, l is 3 and m=n=p=0; and

L is 8-quinolinolate, M is Cu, Ni, Co or Fe, l is 2 or 3 and m=n=p=0.

The invention will be understood more clearly and fully from the following description of certain preferred embodiments.

DETAILED DESCRIPTION OF THE INVENTION

Broadly, the invention relates to a process for the activation of hydrogen peroxide (HOOH) or dioxygen ($O_2$) which comprises contacting hydrogen peroxide or dioxygen with a complex of the formulae shown above under conditions suitable for the activation to take place. Hydrogen peroxide and dioxygen are molecules which, by themselves, do not react with a substrate. Thus, the term "activation" as used herein means imparting to hydrogen peroxide or dioxygen the ability to transform an organic substrate to some new molecule. In accordance with the invention, hydrogen peroxide and dioxygen are activated by contact with a complex according to the invention. Upon contact, hydrogen peroxide and dioxygen, in association with the complex, form species which in turn transform the substrate into a new molecule. Hydrogen peroxide is activated to species 1b shown in equation (2) below. Dioxygen is activated to species 7 shown in equation (12) below. It is to be noted that in species 7, the bond between the two oxygen atoms of dioxygen is not broken. In other words, activation of dioxygen in accordance with the invention involves the formation of an activated species which incorporates dioxygen in such a way that the bond between the two oxygen atoms of dioxygen is preserved.

The complex is an aromatic, heterocyclic ligand (L, L')-metal(M) complex. Advantageously, L and L' are the same or different and each is a ligand of formula

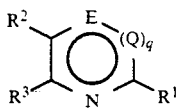

wherein
$R^1$ is hydrogen, $CO_2^-$ or $CO_2H$;
$R^2$ is hydrogen;
$R^3$ is hydrogen, $CO_2^-$, $CO_2H$ or pyridinyl; or
$R^2$ and $R^3$ joined together and taken with the other atoms in the ring form a quinoline ring which is unsubstituted or substituted in the 8-position by $O^-$;
E is CH, N, NH or $CR^4$ wherein $R^4$ is alkyl;
Q is CH;
q is 0 or 1 provided that when q is 0, there is no Q substituent, E and the carbon atom to which $R^1$ is attached are joined directly and E is NH;
M is a transition metal cation;
A is an anion of an organic or mineral acid;
l is 1, 2, 3 or 4;
m is 0 or 1;
n is 0, 1, 2, 3 or 4; and
p is 0, 1 or 2.

More advantageously, L and L' are selected from the consisting of pyridine, 2,2'-bipyridine, pyrazine, imidazole, quinoline, 8-quinolate, picolinate, 2,6-pyridine dicarboxylate, 2-pyrazine carboxylate, 2,6-pyrazine dicarboxylate, 2-imidazole carboxylate and 2,5-imidazole dicarboxylate.

M is a transition metal cation. Transition metals include elements 21–29, 39–47, 57–79 and all known elements from 89 on of the Periodic Table. Advantageously, M is selected from the group consisting of Fe, Mn, Co, Ni Cu and Ru.

A is an anion and advantageously is an anion of an organic or mineral acid or is a halogen ion. More advantageously, A is selected from the group consisting of $ClO_4$, $AcO^-$, $NO_3^-$, $F^-$, $Cl^-$, $Br^-$ and $I^-$. The following are preferred complexes in accordance with the invention:

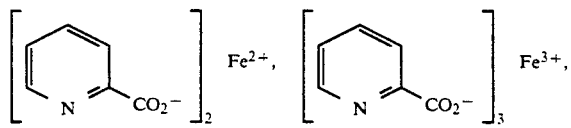

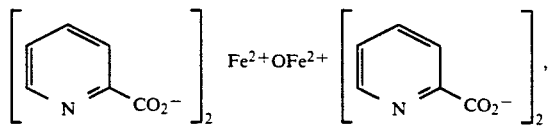

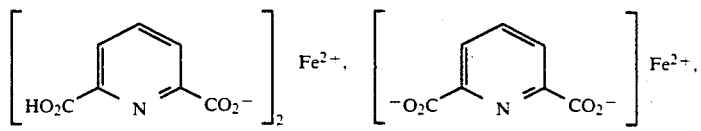

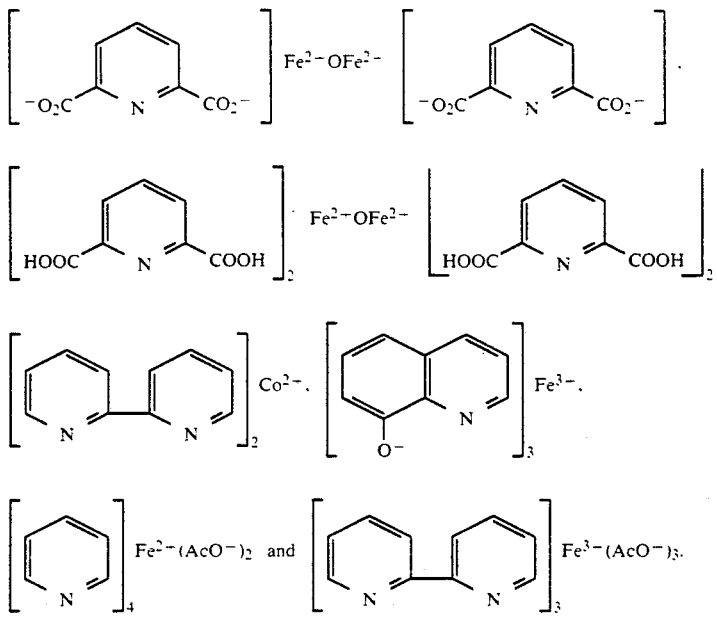

More advantageously, complexes according to the invention are selected from the group consisting of bis(picolinato)-iron(II)[Fe(PA)$_2$], (2,6-dicarboxylatopyridine)-iron(II)[Fe(DPA)], bis(2,6-carboxylatocarboxyl-pyridine)iron(II)[Fe(DPAH)$_2$], the μ-oxo dimers thereof, i.e., (PA)$_2$FeOFe(PA)$_2$, (DPA)-FeOFe(DPA) and (DPAH)$_2$FeOFe(DPAH)$_2$ and bis(bipyridine)cobalt(II)[CO$^{II}$(bpy)$_2{}^{2+}$].

Hydrogen peroxide or dioxygen so activated by the complexes described above can be used to transform a variety of organic compounds. In general, an organic compound is contacted with a complex described above in the presence of hydrogen peroxide or dioxygen under conditions suitable for the transformation (e.g., ketonization of methylenic carbons or dioxygenation) to take place, provided that if the contact is made in the presence of dioxygen, then M in the complex is in its reduced state (e.g., Fe$^{II}$, Cu$^I$, etc.) and R$^1$ and R$^3$ are the same or different and each is CO$_2{}^-$ or CO$_2$H when M is Fe.

Thus, a methylenic carbon contained in an organic compound can be converted to a carbonyl by contacting the organic compound with a complex as described above in the presence of hydrogen peroxide or dioxygen under conditions suitable for the conversion to take place, provided that if the contact is made in the presence of dioxygen, then M in the complex is in its reduced state and R$^1$ and R$^3$ are the same or different and each is CO$_2{}^-$ or CO$_2$H when M is Fe. In one embodiment, the organic compound containing the methylenic carbon has formula I $$R^5-CH_2-R^6 \quad (I)$$

wherein

R$^5$ and R$^6$ are the same or different and each is hydrogen, hydroxyl, alkyl or is aryl which is unsubstituted or mono- or polysubstituted by halogen, NO$_2$, OH, loweralkyl or loweralkoxy, or R$^5$ and R$^6$ taken together form a C$_3$–C$_{13}$ saturated or unsaturated ring, provided R$^5$ and R$^6$ are not both hydrogen, which is converted to a compound of formula II

wherein R$^5$ and R$^6$ are defined as above. In a preferred embodiment, R$^5$ and R$^6$ are the same or different and each is alkyl or aryl.

As used with reference to formulae I and II above, as well as throughout the specification and appended claims, the term "alkyl" refers to a straight or branched chain hydrocarbon radical containing no unsaturation such as, e.g., methyl, ethyl, 1-propyl, 2-propyl, 2-methylpropyl, 1-pentyl, 2-pentyl, 3-hexyl, 4-heptyl, 2-octyl, and the like. The term "alkenyl" refers to a straight or branched chain hydrocarbon radical containing one or more double bonds such as, e.g., propenyl, pentenyl, hexenyl, and the like. The term "alkoxy" refers to a compound formed by the combination of an alkyl group and an oxy group and includes, e.g., methoxy, ethoxy, propoxy, butoxy, and the like. The term "lower" as applied to any of the aforementioned groups refers to a group having a carbon skeleton containing up to and including 6 carbon atoms. The term "halogen" refers to a member of the family consisting of fluorine, chlorine, bromine and iodine. The term "aryl" refers to an organic radical derived from an aromatic or heteroaromatic hydrocarbon by the removal of one hydrogen atom, such as, e.g., phenyl, naphthyl, tolyl, salicyl, pyridinyl, etc. The terms "arylloweralkyl" and "arylloweralkoxy" refer to an aryl radical which is mono- or polysubstituted by loweralkyl or loweralkoxy. The term "polysubstituted" as used herein refers to a molecule which is di- or higher substituted, the degree of substitution being determined by the available sites on the molecule.

Thus, methylenic carbons contained in, e.g., cyclohexane, n-hexane, ethylbenzene, diphenylmethane, 2-methyl-butane, toluene, adamantane, cyclododecane, cyclohexene and 1,4-cyclohexadiene can be converted to carbonyls to yield, respectively, cyclohexanoane, 3-hexanone and 2-hexanone, acetophenone, benzophenone, 3-methyl-2-butanone, benzaldehyde, 2-adamantanone, cyclododecanone, 2-cyclohexene-1-one and 1,4-cyclohexadiene-3-one (which spontaneously converts to phenol).

In another embodiment of the invention, dioxygen or hydrogen peroxide is activated by a complex described above to convert an acetylene to an o-dicarbonyl compound. The acetylene is contacted with the complex in the presence of hydrogen peroxide or dioxygen under conditions suitable for the conversion to take place, provided that if the contact is made in the presence of dioxygen, then M in the complex is in its reduced state and $R^1$ and $R^3$ are the same or different and each is $CO_2^-$ or $CO_2H$ when M is Fe. In particular, an acetylene of formula III

$$R^7-C\equiv C-R^8 \qquad (III)$$

wherein $R^7$ and $R^8$ are the same or different and each is H, halogen, alkyl or is aryl which is unsubstituted or mono- or polysubstituted by halogen, $NO_2$, OH, loweralkyl or loweralkoxy, can be converted to a compound of formula IV

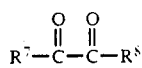

$$\underset{R^7-C-C-R^8}{\overset{O\quad O}{\parallel\;\parallel}} \qquad (IV)$$

wherein $R^7$ and $R^8$ are defined as above. In a preferred embodiment, both $R^7$ and $R^8$ are aryl. For example, in accordance with this embodiment of the invention, diphenylacetylene is converted to benzil.

In still another embodiment of the invention, hydrogen peroxide or dioxygen is activated by a complex described above to convert an aryl olefin to an aldehyde or a ketone. The olefin is contacted with the complex in the presence of hydrogen peroxide or dioxygen under conditions suitable for the conversion to take place, provided that if the contact is made in the presence of dioxygen, then M in the complex is in its reduced state and $R^1$ and $R^3$ are the same or different and each is $CO_2^-$ or $CO_2H$ when M is Fe. In particular, an olefin of formula V

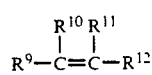

$$\underset{R^9-C=C-R^{12}}{\overset{R^{10}\;R^{11}}{|\quad|}} \qquad (V)$$

wherein $R^9-R^{12}$ are the same or not all the same and each is H, alkyl or is aryl which is unsubstituted or mono- or polysubstituted by halogen, $NO_2$, OH, loweralkyl or loweralkoxy provided at least one of $R^9-R^{12}$ is aryl or substituted aryl, can be converted to compounds of formulae VI and VII

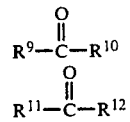

$$\underset{R^9-C-R^{10}}{\overset{O}{\parallel}} \qquad (VI)$$

$$\underset{R^{11}-C-R^{12}}{\overset{O}{\parallel}} \qquad (VII)$$

wherein $R^9-R^{12}$ are as defined above. In a preferred embodiment, $R^9$, $R^{10}$, $R^{11}$ and $R^{12}$ are the same or not all the same and each is H, alkyl or aryl. Thus, for example, cis-stilbene, styrene or methylstyrene can all be converted in accordance with the invention to benzaldehyde (and additionally formaldehyde and acetaldehyde, respectively).

Another embodiment of the invention involves the activation of hydrogen peroxide or dioxygen by a complex described above to convert an aryl-α-diol to a carboxylic acid, a dicarboxylic acid or a dicarboxylic acid anhydride. The aryl-α-diol is contacted with a complex described above in the presence of dioxygen under conditions suitable for the conversion to take place, provided M in the complex is in its reduced state and $R^1$ and $R^3$ are the same or different and each is $CO_2^-$ or $CO_2H$ when M is Fe. Thus, an aryl-α-diol of formula VIII

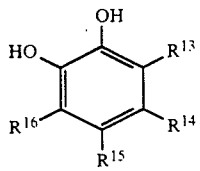

(VIII)

wherein $R^{13}-R^{16}$ are the same or not all the same and each is H, halogen, $NO_2$, CH, or is loweralkyl, aryl, arylloweralkyl, loweralkoxy or arylloweralkoxy each of which is unsubstituted or mono- or polysubstituted by halogen, $NO_2$, OH, loweralkyl, loweralkoxy or $NR^{17}R^{18}$ wherein $R^{17}$ and $R^{18}$ are the same or different and each is H or loweralkyl, can be converted to compounds of formulae IX and X

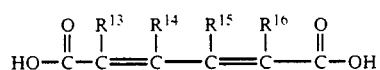

(IX)

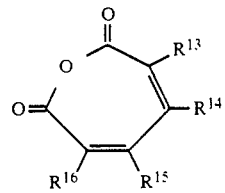

(X)

wherein $R^{13}-R^{16}$ are defined as above. In addition an aryl-α-diol of formula XI

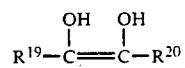

$$\underset{R^{19}-C=C-R^{20}}{\overset{OH\;\;OH}{|\quad\;|}} \qquad (XI)$$

wherein $R^{19}$ and $R^{20}$ are the same or different and each is aryl which is unsubstituted or mono- or polysubstituted by halogen, $NO_2$, OH, loweralkyl, loweralkoxy or $NR^{17}R^{18}$ wherein $R^{17}$ and $R^{18}$ are defined as above, can be converted to compounds of formulae XII, XIII and XIV:

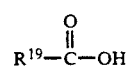

$$\underset{R^{19}-C-OH}{\overset{O}{\parallel}} \qquad (XII)$$

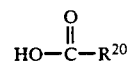

$$\underset{HO-C-R^{20}}{\overset{O}{\parallel}} \qquad (XIII)$$

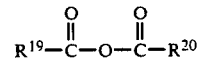

$$\underset{R^{19}-C-O-C-R^{20}}{\overset{O\quad\;\;O}{\parallel\quad\;\parallel}} \qquad (XIV)$$

wherein $R^{19}$ and $R^{20}$ are defined as above. For example, in accordance with the invention, catechol and benzoin can be converted to muconic acid (and its anhydride) and benzoic acid (and its anhydride), respectively. One skilled in the art will recognize that benzoin exhibits enol-keto tautomerism and the enol tautomer is an aryl-α-diol.

Still another embodiment of the invention involves the activation of hydrogen peroxide by a complex described above to oxidize an alcohol or an aldehyde. Thus, an alcohol of formula XV

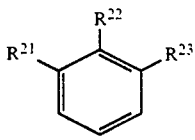
(XV)

wherein $R^{21}$ and $R^{23}$ are the same or different and each is loweralkyl and $R^{22}$ is OH, can be oxidized to a compound of formula XVII

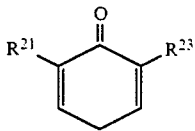
(XVII)

wherein $R^{21}$ and $R^{23}$ are defined as above, or an alcohol of formula XVIII

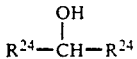
(XVIII)

wherein $R^{24}$ and $R^{25}$ are the same or different and each is hydrogen, alkyl or aryl which is unsubstituted or mono- or poly-substituted by halogen, $NO_2$, loweralkyl or loweralkoxy, or $R^5$ and $R^6$ taken together form a $C_3$-$C_{13}$ saturated or unsaturated ring provided $R^{24}$ and $R^{25}$ are not both hydrogen, can be converted to a compound of formula XIX

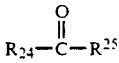
(XIX)

wherein $R^{24}$ and $R^{25}$ are as defined above. In addition, an aldehyde of formula XX

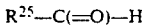
$R^{25}$—C(=O)—H    (XX)

wherein $R^{25}$ is aryl which is unsubstituted or mono- or polysubstituted by halogen, $NO_2$, OH, loweralkyl or loweralkoxy, can be oxidized to a compound of formula XXI

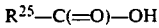
$R^{25}$—C(=O)—OH    (XXI)

wherein $R_5$ is defined as above. For example, in accordance with this embodiment of the invention, 2,6-dimethylphenol, cyclohexanol, benzyl alcohol and benzaldehyde can be oxidized to 2-6-dimethyl-parabenzoquinone, cyclohexanone, benzaldehyde and benzoic acid, respectively.

In yet another embodiment of the invention, a mercaptan can be removed from gas streams and hydrogen sulfide or a mercaptan can be removed from liquid streams by contacting a gas stream containing a mercaptan or a liquid stream containing hydrogen sulfide or a mercaptan with a complex described above in the presence of dioxygen under conditions suitable for the conversion of hydrogen sulfide or the mercaptan to elemental sulphur, provided that M in the complex is in its reduced state and $R^1$ and $R^3$ are the same or different and each is $CO_2^-$ or $CO_2H$ when M is Fe. In general, mercaptan as used herein refers to any organic compound containing the radical-SH. In particular, the mercaptan will have the formula RSH wherein R is alkyl, aryl or arylloweralkyl.

The processes according to the invention are generally carried out in a solvent matrix comprising a an aromatic heterocyclic solvent having at least one nitrogen atom in admixture with (1) an organic or mineral acid or (2) a polar, aprotic, non-basic organic solvent wherein the ratio of the aromatic heterocyclic solvent to the acid or organic solvent in the mixture ranges from about 1-6:6-1. Aromatic heterocyclic solvents include, e.g., pyridine, pyrazine and imidazole and substituted derivatives thereof; organic acids include those which do not contain a methylenic carbon, e.g., acidic acid; mineral acids include, e.g., perchloric acid and hydrochloric acid; and polar, aprotic, non-basic organic solvents include, e.g., acetonitrile (MeCN), benzonitrile and methylene chloride. In the processes of the invention wherein M in the complex is Fe, the solvent matrix advantageously comprises a mixture of pyridine and acetic acid wherein the ratio of pyridine to acetic acid in the mixture is about 2:1. In the processes of the invention wherein M in the complex is Co, the solvent matrix advantageously comprises a mixture of acetonitrile and pyridine wherein the ratio of acetonitrile to pyridine is about 4:1.

In accordance with the invention, the processes are carried out at a temperature from about $-30°$ C. to $80°$ C., advantageously from about $25°$ C. to $60°$ C. and more advantageously from about $20°$ C to $25°$ C. Where the process involves the activation of hydrogen peroxide, the concentration of the substrate broadly ranges from about 0.5 to 5.0M, advantageously from about 0.5 to 1.0M. The concentration of the complex ranges from about 1 to 100 mM. Hydrogen peroxide is used in excess. Generally, the amount of hydrogen peroxide to be used is related to the amount of metal present in the complex and typically the ratio of hydrogen peroxide to metal is about 20:1. Thus, the concentration of hydrogen peroxide can range from about 56 mM to about 1M, advantageously, from about 56 mM to 100 mM for a substrate concentration of 1M.

Where the activation of dioxygen is involved, the complex can be added to the point of saturation since the reaction rate is linear with the concentration of complex (catalyst). Typically, the concentration of catalyst ranges from about 1 to 100 mM. The source of dioxygen can be either pure dioxygen or air. If the source of dioxygen is pure dioxygen, the pressure used is generally limited by the vessel being used but nevertheless can range from about 1 atmosphere to 100 atmospheres. Typically, a pressure of 1 atmosphere provides 3.4 mM dioxygen. In contrast, 1 atmosphere air provides 0.68 mM dioxygen. Accordingly, reactions using pure dioxygen are approximately 5 times as fast as reactions using air.

In the processes of the invention which involve the activation of dioxygen, a reductant is advantageously used. Generally, the reductant is hydrogen sulfide, a mercaptan, a hydrazine or cyclohexadiene (1,3- and 1,4-). Advantageously, the reductant is selected from the group consisting of hydrazine, 1,2-diphenylhydrazine, benzyl mercaptan and hydrogen sulfide. There is no limit on the amount of reductant that can be used and generally the more used, the better. Typically, the concentration of the reductant ranges from about 10 mM to 100M for a substrate concentration of about 1M.

Another embodiment of the invention is directed to novel complexes of formula

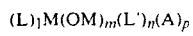

wherein:

L and L' are the same or different and each is a ligand of formula

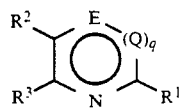

wherein
- $R^1$ is hydrogen, $CO_2^-$ or $CO_2H$;
- $R^2$ is hydrogen;
- $R^3$ is hydrogen, $CO_2^-$, $CO_2H$ or pyridinyl; or
- $R^2$ and $R^3$ joined together and taken with the other atoms in the ring form a quinoline ring which is unsubstituted or substituted in the 8-position by $O^-$;
- E is CH, N, NH or $CR^4$ wherein $R^4$ is alkyl;
- Q is CH;
- q is 0 or 1 provided that when q is 0, there is no Q substituent, E and the carbon atom to which $R^1$ is attached are joined directly and E is NH;
- M is a transition metal cation;
- A is an anion of an organic or mineral acid;
- l is 1, 2, 3 or 4;
- m is 0 or 1;
- n is 0, 1, 2, 3 or 4; and
- p is 0, 1 or 2; excluding complexes wherein:
- L is pyridine, M is Cu or Mn, A is $Cl^-$, $Br^-$, $I^-$, $Cl^-$, $ClO_4^-$ or $NO_3^-$, l is 2, m=n=0 and p is 1;
- L is pyridine, M is Fe, A is $Cl^-$, l is 4, m=n=0 and p is 2;
- L is 2,2'-bipyridine, M is Cu or Mn, A is $Cl^-$, $Br^-$, $I^-$, $Cl^-$, $ClO_4^-$ or $NO_3^-$, l is 1, m=n=0 and p is ;
- L is 2,2'-bipyridine, M is Ru, l is 3 and m=n=p=0;
- L is picolinate, M is Fe, l is 3 and m=n=p=0; and
- L is 8-quinolinolate, M is Cu, Ni, Co or Fe, l is 2 or 3 and m=n=p=0.

Further details concerning the various substituents and certain preferred embodiments of the complexes are given above with regard to process embodiments of the invention and therefore will not be repeated here.

The invention will be more fully described and understood with reference to the following examples which are given by way of illustration and to Schemes I, II and III below. In the examples, the reaction products were separated and identified with a Hewlett-Packard 5880A Series gas chromatograph equipped with a HP-1 capillary column (cross-linked methyl silicone gum phase, 12 m × 0.2 mm i.d.) and by gas chromatography-mass spectrometry (Hewlett-Packard 5790A Series gas chromatograph with mass-selective detector). Reference samples were used to confirm product identification. The quantities of products were calculated from standard curves for authentic samples. Direct injections of the product solution (1–2 μL) were made.

Cyclic voltammetry was accomplished with a Bioanalytical Systems Model CV-27 voltammograph and a Houston Instruments Model 200 XY recorder. Controlled-potential electrolysis was performed with a three-electrode potentiostat (Princeton Applied Research Model 173 potentiostat/galvanostat, Model 175 universal programmer, and Model 179 digital coulometer). A Vacuum Atmospheres inert-atmosphere glovebox was used for storage, preparation, and addition of the superoxide species.

The UV/vis spectrophotometric measurements were performed on a Hewlett-Packard Model 8450 diodearray spectrophotometer. Infrared spectra were recorded with an IBM IR/44 (IR/40S Spectrometer with IR/30S upgrade unit) FTIR instrument. Solid-state samples were made using a KBr pellet press. Solid magnetic suceptibility measurements were performed with a Johnson Matthey Model MSB1 Magnetic Susceptibility Balance.

Singlet dioxygen production was detected by measurement of its characteristic 1268-nm chemiluminescence. The chemiluminescence spectrometer that was used for these measurements has been described (9). Singlet oxygen-quenching constants for the iron complexes were derived from $^1O_2$-phosphorescence measurements as previously described in the literature (10).

The solvents for the syntheses and analyses were the highest purity commercially available and were used without further purification. Burdick and Jackson "distilled in glass" grade acetonitrile (MeCN, 0.004% $H_2O$), dimethylformamide (DMF, 0.01%, $H_2O$), pyridine (py, 0.014% $H_2O$), and glacial acetic acid (HOAc, ACS grade, Fisher Chemical Co.) were used as solvents. The magnetic susceptibility measurements made use of $d_7$-DMF that contained 1% tetramethylsilane (TMS, Aldrich Chemical Co.). High purity argon gas was used to deaerate the solutions. All compounds were dried in vacuo over $CaSO_4$ for 24 hours prior to use.

Bold face Arabic numerals which may or may not be followed by a bold face, lower case letter and which are in parenthesis refer to compounds shown in Schemes I, II and III below.

EXAMPLE I

Preparation of Reagents

A. Synthesis of Concentrated Hydrogen Peroxide

Water was Carefully removed from 10 mL of 50% HOOH at 0° C. via high-vacuum evaporation to give 1.5–3 mL of almost pure hydrogen peroxide (HOOH) (7). This was quickly dissolved in dry acetonitrile (25 mL). The resulting solutions were assayed by iodometric titration, and found to be 1.6M (94% HOOH) and 3.6M (82% HOOH).

B Synthesis of Tetramethylammonium Picolinate And Tetramethylammonium Dipicolinate Tetramethylammonium picolinate [$(Me_4N)PA$] and bis(tetramethylammonium) 2,6-dicarboxylato-pyridine [$(Me_4N)_2DPA$] were prepared by the neutralization of picolinic acid (PAH) and 2,6-pyridinedicarboxylic acid ($DPAH_2$), respectively, with tetramethylammonium hydroxide in methanol solution (Aldrich). $(Me_4N)PA$ was recrystallized from acetonitrile and $(Me_4N)_2DPA$ from 95% MeCN/5% MeOH. The hydroscopic products were stored under vacuum, and were used to prepare 50 mM stock solutions in the appropriate solvent mixture.

C. Synthesis of [Fe(MeCN)$_4$](ClO$_4$)$_2$

The [Fe(MeCN)$_4$](ClO$_4$)$_2$ complex was prepared by multiple recrystallizations of [Fe(H$_2$O)$_6$(ClO$_4$)$_2$] (G.F. Smith Chemicals) from MeCN.

D. Preparation of Iron Picolinate And Iron Dipicolinate Solutions

Solutions of Fe(PA)$_2$, Fe(PA)$_3$, Fe(DPA), and Fe(DPAH)$_2$ were prepared in situ by mixing [Fe(MeCN)$_4$](ClO$_4$)$_2$ or Fe(ClO$_4$)$_3$ (anhydrous) with various ratios of the ligand anion. Fe(PA)$_2$ has a single absorption band [DMF; $\lambda_{max}$, 462 nm ($\epsilon$ 1200 cm$^{-1}$M$^{-1}$) and in 2Py/HOAc; $\lambda_{max}$, 402 nm ($\epsilon$ 2480 cm$^{-1}$M$^{-1}$)], which shifts to a longer wavelength with excess ligand [Fe(PA)$_3$$^-$ in DMF; $\lambda_{max}$, 496 nm ($\epsilon$ 1670 cm$^{-1}$M$^{-1}$)]. Likewise, Fe(DPA) has a single absorption band [DMF; $\lambda_{max}$, 484 nm ($\epsilon$ 620 cm$^{-1}$M$^{-1}$) and in 2py/HOAc: $\lambda_{max}$, 395 cm ($\epsilon$ 1950 cm$^{-1}$M$^{-1}$) with two shoulders [480 nm ($\epsilon$ 1280 cm$^{-1}$M$^{-1}$) and 500 nm ($\epsilon$ 840 cm$^{-1}$M$^{-1}$)]. The band shifts with the addition of excess ligand [(Fe(DPA)$_2$$^{2-}$ in DMF; $\lambda_{max}$, 552 nm ($\epsilon$ 540 cm$^{-1}$M$^{-1}$)].

E. Syntheses of "Fe(PA)$_2$", [(PA)$_2$Fe(OH)]$_2$ (1a in Scheme I below), [(PA)$_2$FeOFe(PA)$_2$](1b in Scheme I below), "Fe(DPA)" and [(DPA)Fe(OH)]$_2$ The nominal complexes "Fe(PA)$_2$" and "Fe(DPA)" were prepared by mixing [(Fe(MeCN)$_4$](ClO$_4$)$_2$ and the stoichiometric amount of the tetramethylammonium salt of the ligand (in acetonitrile under argon), which yielded a brick-red precipitate. The isolated powder gradually turned light brown upon exposure to air. This brown powder ["Fe(PA)$_2$"], when dissolved in DMF, exhibited a broad absorption band [$\lambda_{max}$, 348 nm ($\epsilon$ 1400 cm$^{-1}$M$^{-1}$) and the solid had infrared bands at 695, 708, 761, 950, 1025, and 1049 cm$^{-1}$ with a strong, broad band at 1092 cm$^{-1}$. The ligand, (Me$_4$N)PA, exhibited bands at 689, 774, and 834 cm$^{-1}$ with a broad band at 981 cm$^{-1}$ and small bands at 1034 and 1077 cm$^{-1}$). The precipitate obtained for "Fe(DPA)" was an orange-brown powder that became light brown upon exposure to air. Dissolution of "Fe(PA)$_2$" and "Fe(DPA)" in DMF and electrochemical characterization confirmed that the materials were each about ⅔ in their reduced states [Fe(PA)$_2$ and Fe(DPA)].

Exposure of MeCN solutions of Fe(PA)z to air resulted in the precipitation of a pale green powder, [(PA)$_2$Fe(OH)]$_2$(1a), which in py/HOAc solution exhibited an absorption edge below 400 nm [$\lambda_{max}$, 350 nm ($\epsilon$ 2260 cm$^{-1}$M$^{-1}$)]. The solid had infrared bands at 694, 708, 760, 857, 1020, and 1047 cm$^{-1}$, and a magnetic moment, $\mu_\beta$, of 7.0 B.M. per dimer molecule (or 4.9 B.M. per Fe). In DMF, 1a had a magnetic moment (Evan's method) (11) Of 3.6±0.3 B.M. per dimer (2.5 B.M. per Fe), an irreversible reduction at −0.65 V vs SCE., and a strong UV absorption band [$\lambda_{max}$, 350 nm ($\epsilon$ 3100 cm$^{-1}$M$^{-1}$)]. The elemental analysis of the pale green powder, [(PA)$_2$Fe(OH)]$_2$ (1a), was performed by Galbraith Laboratories, Inc. (Anal. Calcd for C$_{24}$H$_{18}$N$_4$O$_{10}$Fe$_2$:C, 45.46; H, 2.86; N, 8.84; 0, 25.23; Fe, 17.61; Found: C, 45.17; H, 3.08; N, 8.80, 0, 25.31; Fe, 16.93).

The 1:1 combination of Fe(PA)$_3$ and (Me$_4$N)OH 5H$_2$O in DMF gave a golden-brown solution of a product species, (PA)$_2$FeOFe(PA)$_2$ (1b), with a magnetic moment of 3.1±0.2 B.M. per dimer (2.2 B.M. per Fe), an irreversible reduction potential at −0.85 V vs SCE, and a strong UV absorption band [$\lambda_{max}$, 350 nm ($\epsilon$ 3300 cm$^{-1}$M$^{-1}$).

F. Synthesis of [(Ph$_3$PO)$_4$FeOOFe(OPPh$_3$)$_4$(ClO$_4$)$_4$

The synthesis and characterization of this complex has been described in the literature (12). Tetramethylammonium superoxide [(Me$_4$N)O$_2$] was prepared by combination of KO$_2$ (Aldrich) and (Me$_4$N)OH.5H$_2$O (Fluka) (13, 14). The (py)$_4$FeCl$_2$ complex was prepared by multiple recrystallizations of FeCl$_2$.4H$_2$O (Mallinckrodt) in dry pyridine. Combination of (py)$_4$FeCl$_2$ and AgOAc (Strem) in dry pyridine gave a white AgCl precipitate, which was removed prior to the evaporation of the filtrate to give (py)$_4$Fe(OAc)$_2$. The [Fe(OPPh$_3$)$_4$](ClO$_4$)$_2$ complex was synthesized from [Fe(MeCN)$_4$](ClO$_4$)$_2$ and triphenylphosphine oxide (15).

G. Synthesis of Co$^{II}$(bpy)$_2$$^{2+}$

The nominal complex Co$^{II}$(bpy)$_2$$^{2+}$ was prepared by mixing two equivalents of bipyridine and one equivalent of cobalt perchlorate in a stock solution of acetonitrile in argon. The resulting precipitate was filtered and dried.

EXAMPLE II

Hydrogen Peroxide Activation By Various Iron Complexes For The Conversion Of Various Substrates For activation of HOOH by the various iron complexes, solutions that contained 0.5–1.0M substrate and 1–20 mM iron complex in 3.5 mL of a pyridine/acetic acid mixture were used. Hydrogen peroxide (56 mM or 100 mM) was injected as an anhydrous solution in MeCN or as undiluted 50% HOOH in water. After 4 h with constant stirring at room temperature (22+±2° C.), samples of the reaction solution were injected into a capillary-column gas chromatograph for analysis. In some cases the reaction was quenched with water, and the product solution was extracted with diethyl ether. Product species were characterized by GC-MS. Reference samples were used to confirm product identifications, and to produce standard curves for quantitative assays of the product species.

A. Conversion of Cyclohexane

Hydrogen peroxide (HOOH) was added to pyridine/acetic acid solutions that contained several iron-picolinate (PA), iron-(2,6-dicarboxylatopyridine)(DPA), and iron-(8-quinolinolate) (8-Q) complexes, resulting in the catalyzed transformation of c-C$_6$H$_{12}$ to cyclohexanone [c-C$_6$H$_{10}$(O)]. The substrate and each of the complexes were combined in 3.5 mL of pyridine/acetic acid solvent (2:1 mol-ratio), followed by the slow addition over a period of one to two minutes of 13 μl of 17.3M HOOH (49%) in water to give 56 mM-96 mM HOOH. The reactions were stirred at 20° to 24° C. for 4 to 15 hours. The product solutions were analyzed by capillary gas chromatography and GC-MS, either by direct injection of the product solution or by quenching with water and extracting with diethyl ether. Table IA summarizes the conversion efficiencies (c-C$_6$H$_{12}$ oxidized per two HOOH) and product yields for the catalyzed oxygenation of cyclohexane by HOOH and compares the various complexes in terms of catalytic efficiency, turnover and product selectivity in a pyridine/acetic acid solution matrix. An efficiency of 100% represents one substrate oxygenation per two HOOH molecules added; the remainder of the HOOH was unreacted or consumed via slow $O_2$ evolution and Fenton Chemistry to produce $[py(OH)]_n$. Catalyst turnover was calculated as moles of substrate oxygenated per mole of catalyst (complex). No reactions occurred when $[Fe(MeCN)_4](ClO_4)_2$, $(py)_4Fe(OAc)_2$, and Fe(acac)$_2$ were used as catalysts. In addition, $(py)_4FeCl_2$, $(bpy)_3Fe(ClO_4)_2$ and $FeCl_3$ gave reaction efficiencies of less than 15%, with cyclohexanol as the major product. The effects of the solvent matrix on the yields of the c-$C_6H_{12}$/HOOH/Fe(PA)$_2$ reaction system are summarized in Table IB.

lated. 100% reaction efficiency represents one substrate oxygenation per two HOOH molecules added; the remainder of the HOOH was either unreacted or consumed via slow $O_2$ evaluation and Fenton Chemistry to produce $1/n[py(OH)_n]$.

TABLE I

Products and Conversion Effeciencies for the Iron-Catalyzed Ketonization of Cyclohexane by HOOH in Various Solvents.

A. Cyclohexane (1M); 96 mM HOOH; pyridine/HOAc (2:1 mol ratio)

| iron catalysts (3.3 mM) | reactn efficiency, % (±3) | catalyst turnovers | products cyclohexanone, % (±4) | cyclohexanol, % (±4) |
|---|---|---|---|---|
| Fe(PA)$_2$ | 72 | 11 | 93 | 7 |
| Fe(PA)$_2$; (56 mM HOOH) | 72 | 6 | 95 | 5 |
| Fe(PA)$_2$; (56 mM HOOH); 101 mM H$_2$O | 58 | 5 | 94 | 6 |
| 0.9 mM Fe(PA)$_2$; (56 mM HOOH) | 71 | 23 | 94 | 6 |
| 0.9 mM Fe(PA)$_2$; (56 mM HOOH); 101 mM H$_2$O | 17 | 5 | 94 | 6 |
| (PA)$_2$FeOFe(PA)$_2$(1) (1.7 mM) | 72 | 11 | 93 | 7 |
| Fe(PA)$_3$ | 64 | 10 | 85 | 15 |
| Fe(PA)(ClO$_4$) | 65 | 9 | 94 | 6 |
| Fe(DPA) | 73 | 12 | >97 | <3 |
| (DPA)FeOFE(DPA) (5) (1.7 mM) | 76 | 13 | >97 | <3 |
| Fe(8-Q)$_3$ | 47 | 7 | 90 | 10 |

B. Cyclohexane (1M); 3.5 mM Fe(PA)$_2$; 56 mM HOOH

| Solvent | reactn efficiency, % (±3) | products cyclohexanone, % (±4) | cyclohexanol, % (±4) |
|---|---|---|---|
| pyridine (py) | 6 | 93 | 7 |
| py/HOAc (4.5:1 mol-ratio) | 65 | 93 | 7 |
| py/HOAc (1.9:1 mol-ratio) | 72 | 93 | 7 |
| py/HOAc (1.0:1 mol-ratio) | 66 | 93 | 7 |
| py/HOAc (0.6:1 mol-ratio) | 58 | 93 | 7 |
| MeCN | 9 | 40 | 60 |
| MeCN/HOAc (3.6:1 mol-ratio) | 11 | 73 | 27 |

The presence of substantial amounts of water (100 mM) reduced the reaction efficiency (especially for low Fe(PA)$_2$ concentrations), but did not reduce the selectivity for ketone formation. The use of acetonitrile in place of the pyridine/HOAc solvent system greatly reduced the reaction efficiency and eliminated any selectivity. With pure pyridine as the solvent, there was no reactivity. In the absence of substrate the Fe(PA)$_2$/HOOH/(py$_2$/HOAc) system slowly decomposed to give $O_2$, $H_2O$, and $[py(OH)]_n$ (half-life >6 h).

B. Conversion of Hydrocarbons With Methylenic Carbons, Acetylenes and Olefins Table II summarizes the conversion efficiencies and product yields for the oxygenation by the HOOH/Fe(PA)$_2$ combination of several organic substrates (hydrocarbons with methylenic carbons, acetylenes, and arylolefins). The substrate and Fe(PA)z were combined in 3.5 mL of pyridine/acetic acid solvent (2:1 mol-ratio), followed by the slow addition over a one to two minute period of 13 μL of 17.3M hydrogen peroxide (49%) in water or 60 μL of 1.6–3.8M hydrogen peroxide (92%) in MeCN to give 56 mM hydrogen peroxide. The mixture was stirred for four hours at 20° to 24° C. The product solution was analyzed by capillary gas chromatography and GC-MS, either by direct injection of the product or by quenching with water and extracting with diethyl ether. Catalyst turnovers (moles of substrate oxygenated per mole of catalyst) are also tabu-

TABLE II

Products and Conversion Efficiencies for the Fe(PA)$_2$-catalyzed (3.5 mM) Ketonization of Methylenic Carbon and the Dioxygenation of Acetylenes and Arylolefins by HOOH (56 mM) in Pyridine/HOAc (2:1 mol-ratio).

| substrate (1M) | reactn efficiency, % (±3) | catalyst turnovers | products |
|---|---|---|---|
| cyclohexane | 72 | 6 | cyclohexanone (97%), cyclohexanol (3%) |
| n-hexane | 52 | 4 | 3-hexanone (53%), 2-hexanone (46%), 1-hexanol (<2%) |
| PhCH$_2$CH$_3$ | 51 | 5 | PhC(O)CH$_3$ (>96%) |
| PhCH$_2$Ph(0.6M) | 35 | 3 | PhC(O)Ph(>96%) |
| PhCH$_3$ | ·9 | <1 | PhCH(O)(>96%) |
| 2-methyl-butane | 32 | 3 | 3-methyl-2-butanone (>95%), 2-methyl-1-butanol (<2%) |
| adamantane (0.1M) | 32 | 3 | 2-adamantanone (43%), 1-adamantanol (29%), 1-pyridinyl-adamantane (two isomers, 18% and 10%) |
| cyclododecane (0.5M) | 70 | 6 | cyclododecanone (90%), cyclododecanol (10%) |
| cyclohexene | 59 | 5 | 2-cyclohexene-1-one (>95%) |
| 1,3-cyclohexadiene | 33 | 5 | PhH (>95%) |
| 1,4-cyclohexadiene | 30[70] | 3[11] | PhOH (17%) [PhH] (83%) |

TABLE II-continued

Products and Conversion Efficiencies for the Fe(PA)₂-catalyzed (3.5 mM) Ketonization of Methylenic Carbon and the Dioxygenation of Acetylenes and Arylolefins by HOOH (56 mM) in Pyridine/HOAc (2:1 mol-ratio).

| substrate (1M) | reactn efficiency, % (±3) | catalyst turnovers | products |
|---|---|---|---|
| cyclohexanone | 0 | | |
| cyclohexanol | 25 | 4 | cyclohexanone (>95%) |
| PhC≡CPh (0.6M) | 40 | 3 | PhC(O)C(O)Ph (>97%) |
| c-PhCH=CHPh | 36 | 4 | PhCH(O) (75%), $\overset{O}{\underset{\diagup\ \diagdown}{\text{PhCHCHPh}}}$ (25%) |
| t-PhCH=CHMe | 48 | 4 | PhCH(O) (63%), $\overset{O}{\underset{\diagup\ \diagdown}{\text{PhCHCHMe}}}$ (16%), two others (21%) |

The relative reaction efficiencies for cyclohexane, n-hexane, cyclohexene, and 1,4-cyclohexadiene were roughly proportional to the number of (<CH₂) groups per molecule, 6, 4, 4, and 2, respectively, and the product for each is the ketone from the transformation of a single methylenic carbon. Addition of a second 56 mM increment of HOOH to a reacted cyclohexane system resulted in an additional ketonization (68% reaction efficiency). The conversion of 1,4-cyclohexadiene to phenol (via ketonization of a methylenic carbon) without any epoxide formation confirmed the selectivity of the reactive intermediate. Likewise, the ketonization of cyclohexene further supported the selective reactivity towards methylenic carbon. However, 1,3-cyclohexadiene was dehydrogenated to give benzene.

The lower reactivity of cyclohexanol relative to cyclohexane ($\sim\frac{1}{3}$) indicates that c-$C_6H_{11}$OH is not an intermediate for the ketonization of c-$C_6H_{11}H_{12}$. This is further supported by the results for a combined substrate of 1M c-$C_6H_{12}$ and 1M c-$_6H_{11}$OH, which had a ketonization efficiency of 65% (in contrast to 72% for 1M c-$C_6H_{12}$ alone, Table II). Likewise, the presence of 1M i-PrOH with 1M c-$C_6H_{12}$ caused a reduction in the conversion efficiency for c-$C_6H_{12}$ to 56%, but no acetone. Analysis of the product solution during the course of the ketonization of 1M c-$C_6H_{12}$ gave a constant 19:1 c-$C_6H_{10}$(O)/c-$C_6H_{11}$OH ratio (0.1 to 1.0 fractional reaction).

The reactive intermediate dioxygenates acetylenes to give the α-dione as the sole product. With the Fe(PA)₂-/HOOH/(py₂/HOAc) system, arylolefins were dioxygenated and epoxidized. Table IIIA provides a comparison of HOOH, m-ClPhC(O)OOH, and t-BuOOH as oxygenation agents for cis-PhCH=CHPh and PhC≡CPh. Hydrogen peroxide is uniquely effective with Fe(PA)₂ for the dioxygenation of these substrates.

TABLE III

Comparison of Hydroperoxides (ROOH) and Iron Catalysts for the Oxygenation of cis-Stilbene (cis-PhCH=CHPh), PhC≡CPh, and c-$C_6H_{12}$ in Pyridine/Acetic Acid (2:1 mol-ratio).

A. 56 mM Hydroperoxide (ROOH); 3.5 mM Fe(PA)₂
1. cis-PhCH=CHPh (1M)

| | | products | |
|---|---|---|---|
| ROOH | reactn efficiency, % (±3) | PhCH(O), % (±4) | $\overset{O}{\underset{\diagup\ \diagdown}{\text{PhCH—CHPh}}}$, % (±4) |
| HOOH | 36 | 75 | 25 |
| m-ClPhC(O)OOH | 11 | 45 | 55 |
| t-BuOOH | 6 | 6 | 94 |

2. PhC≡CPh (1M)

| ROOH | reactn efficiency, % (±3) | products |
|---|---|---|
| HOOH | 40 | PhC(O)C(O)Ph (>97%) |
| m-ClPhC(O)OOH | 10 | PhC(O)C(O)Ph (>97%) |
| t-BuOOH | 0 | |

B. cis-PhCH=CHPh (0.7M); HOOH (15 mM)

| | | products | |
|---|---|---|---|
| catalyst (15 mM) | reactn efficiency, % (±3) | PhCH(O), % | $\overset{O}{\underset{\diagup\ \diagdown}{\text{PhCH—CHPh}}}$, % |
| Fe(PA)₂ | 13 | 59 | 41 |
| (PA)₂FeOFe(PA)₂ | 18 | 52 | 48 |

C. c-$C_6H_{12}$ (1M); HOOH (19 mM)

| catalyst (19 mM) | reactn efficiency, % (±3) | c-$C_6H_{10}$(O), % | (c-$C_6H_{11}$)₂, % | py-$C_6H_{11}$, % |
|---|---|---|---|---|
| (PA)₂Fe | 53 | 20 | 14 | 66 |
| (PA)₂Fe(9 mM) (9 mM HOOH) | 85 | 34 | 3 | 63 |
| (PA)₂Fe(catalyst added to [S]/HOOH) | 67 | 36 | 10 | 54 |
| (PA)₂FeOFe(PA)₂ | 39 | 30 | 13 | 57 |

EXAMPLE III

Activation of Dioxygen by Fe$^{II}$(DPAH)₂ for the Ketonization Of Methylenic Carbons and the Dioxygenation of Acetylenes, Arylolefins and Catechols For activation of dioxygen and conversion of various substrates, the substrate and Fe$^{II}$(DPAH)₂ were combined in 3.5 mL pyridine/acetic acid solvent (2:1 mol-ratio), followed by the addition of dioxygen ($O_2$) at one atmosphere (3.4 mM), in a reaction cell having 6 mL of head-space. The reaction was stirred at a temperature ranging from 20° to 24° for a period of four hours (12 hours for 32 mM $Fe^{II}(DPAH)_2$). Product solutions were analyzed by capillary gas chromatography and GC-MS, either by direct injection of the product solution or by quenching with water and extracting with diethyl ether. The reactions were monitored by UV-visible spectrophotometry and the apparent reaction orders and rate constant were determined from the initial rates of disappearance and appearance of $Fe^{II}(DPAH)_2$ ($\lambda_{max}$, 394 nm). The products and reaction efficiencies for various concentrations of $Fe^{II}(DPAH)_2$ and substrates are summarized in Table IV. In the table, a 100% reaction efficiency represents one substrate ketonization or dioxygenation per $(DPAH)_2FeOOFe(DPAH)_2$ reactive intermediate.

In absence of substrate, the active catalyst was rapidly autoxidized to $(DPAH)_2FeOFe(DPAH)_2$ [$4Fe^{II}(DPAH)_2$ per $O_2$; the apparent second-order rate constant, $k_{ox}$, had a value of $1.3\pm0.5 M^{-1}s^{-1}$ ($k_{obs}/4$)]. The oxidized catalyst [$(DPAH)_2FeOFe(DPAH)_2$] was rapidly reduced to $Fe^{II}(DPAH)_2$ by $PhNHNHPh$, $H_2NNH_2$, $PhCH_2SH$, and $H_2S$ ($k_{red}$: $6.5\pm0.5 M^{-1}s^{-1}$, $0.6\pm0.3 M^{-1}s^{-1}$, $0.5\pm0.3 M^{-s-1}$ and $2.8\pm0.5 M^{-1}s^{-1}$, respectively) to give $PhN=NPh$, $N_2$, $PhCH_2SSCH_2Ph$, and elemental sulfur ($S_8$), respectively. The PhNHNHPh reductant is an effective reaction mimic for the reduced flavin cofactors in xanthine oxidase and cytochrome P-450 reductase. (16)

Addition of $PhNHNHPh$, $H_2NNH_2$, $PhCH_2SH$, or $H_2S$ to the reaction system [$O_2/Fe(DPAH)_2$/substrate in $py_2/HOAc$] reduced the oxidized catalyst [$(DPAH)_2FeOFe(DPAH)_2$] and thereby recycled it for activation of $O_2$ to the reactive intermediate (Table IVA and equation 2 below). Thus, without added reductant 32 mM $(DPAH)_2Fe^{II}$ activated $O_2$ to oxygenate $c$-$C_6H_{12}$ to give 4.4 mM $c$-$C_6H_{10}(O)$, but with 32 mM PhNHNHPh present, 9.9 mM $c$-$C_6$-$H_{10}(O)$ was produced (and 32

TABLE IV

Ketonization of Methylenic Carbons, and Dioxygenation of Arylolefins, Acetylenes and Catechols Via the $Fe^{II}(DPAH)_2$-Induced Activation of Dioxygen in 1.8:1 py/HOAc.

A. Cyclohexane (1M); $O_2$ (1 atm, 3.4 mM)

| $[Fe^{II}(DPAH)_2]$, mM | [reductant], mM | [product], mM $c$-$C_6H_{10}(O)$ | $C$-$C_6H_{11}OH$ | reactn efficiency, % ($\pm 3$) |
|---|---|---|---|---|
| 8 | 0 | 1.1 | <0.05 | 28 |
| 32 | 0 | 4.4 | <0.1 | 28 |
| 83 | 0 | 10.4 | <0.2 | 25 |
| 32 | 32 (PhNHNHPh) | 9.9 | <0.2 | 62 |
| 32 | 64 (PhNHNHPh) | 15.4 | <0.2 | 96 (4 turnovers; each 17% efficient) |
| 3 | 10 (PhNHNHPh) | 2.0 | <0.1 | 133 |
| 3 | 100 (PhNHNHPh) | 20.9 | <0.2 | 1393 (67 turnovers; each 21% efficient) |
| 32 | 16 ($H_2NNH_2$) | 6.7 | <0.2 | 42 |
| 32 | 32 ($H_2NNH_2$) | 9.1 | <0.2 | 57 |
| 32 | 32 ($PhCH_2SH$) | 8.6 | <0.2 | 54 |
| 32 | 128 ($PhCH_2SH$) | 18.5 | <0.2 | 116 (4 turnovers; each 23% efficient) |
| 32 | 10 ($H_2S$) | 5.5 | <0.1 | 34 (1 turnover; 7% efficient) |
| 32 | 62 ($H_2S$) | 7.2 | <0.2 | 45 |
| 14 | 225 ($H_2S$) | 10.0 | <0.2 | 143 (32 turnovers; each 35% efficient) |

B. $Fe^{II}(DPAH)_2$ (32 mM); $O_2$ (1 atm, 3.4 mM)

| substrate | products (mM) | reactn efficiency, % ($\pm 3$) |
|---|---|---|
| $c$-$C_6H_{12}$ (1M) | $c$-$C_6H_{10}(O)$ (4.4) | 28 |
| $PhCH_2CH_3$ (1M) [+128 mM PhNHNHPh] | $PhC(O)CH_3$ (3.5) $PhC(O)CH_3$ (3.5) [18.9] | 22 |
| 2-Me-butane (1M) [+128 mM] PhNHNHPh] | $Me_2CHC(O)Me$ (1.0) $Me_2CHC(O)Me$ (1.0) [9.1] | 6 |
| cyclohexene (1M) | 2-cyclohexene-1-one (1.2) | 7 |
| $PhC\equiv CPh$ (0.6M) | $PhCH(O)C(O)Ph$ (2.2) | 14 |
| $c$-$PhCH=CHPh$ (1M) | $PhCH(O)$ (3.1) | 10 |
| 1,2-$Ph(OH)_2$ (1M) | $HOC(O)CH=CH-CH=CHC(O)OH$ (and its anhydride) (2.0) | 13 |
| $PhCH(OH)C(O)Ph$ (0.3M) | $PhC(O)OH$(5.2) | 16 |
| PhNHNHPh (100 mM) | $PhN=NPh$ (100) | 667 |
| $PhCH_2SH$ (128 mM) | $PhCH_2SSCH_2Ph$ (64) | 800 |
| $H_2S$ (128 mM) | $S_8$ (16.0) | 800 | mM PhN=NPh in two catalytic turnovers). Similar results were obtained with other reductants. When 3 mM $Fe^{II}(DPAH)_2$ was used in combination with 100 mM PhNHNHPh, the rate for the ketonization of c-$C_6H_{12}$ was reduced by an order of magnitude, but each cycle remained about 21% efficient and there were about 67 catalytic turnovers within 12 h (Table IVA).

The dioxygenation of unsaturated α-diols (catechol and benzoin, Table IVB) by the $O_2/Fe^{II}(DPAH)_2$ system parallels that of the catechol dioxygenase enzymes, which are non-heme iron proteins (17). Hence, the reactive intermediate of the $Fe^{II}(DPAH)_2/O_2$ reaction (eq. 1) may be a useful model and mimic for the activated complex of dioxygenase enzymes (18).

This system also affords the means to the selective autoxidation (oxygenation) of hydrocarbon substrates (e.g., c-$C_6H_{12}$) via the coprocessing of $H_2S$ (or RSH)-contaminated hydrocarbon streams. Thus, the combination of c-$C_6H_{12}$ and $H_2S$ with $Fe^{II}(DPAH)_2$ and $O_2$ in a py$_2$/HOAc solvent matrix yielded c-$C_6H_{10}(O)$ and $S_8$, which are marketable products. The data of Table IV indicate that the approximate reaction stoichiometry is 28 $H_2S$ molecules (or 8 $PhCH_2SH$ or 4 PhNHNHPh molecules) oxidized per c-$C_6H_2$ ketonization

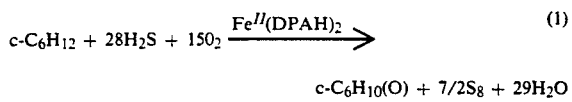

$$c\text{-}C_6H_{12} + 28H_2S + 15O_2 \xrightarrow{Fe^{II}(DPAH)_2} \quad (1)$$

$$c\text{-}C_6H_{10}(O) + 7/2S_8 + 29H_2O$$

In a flow-reactor for coprocessing hydrocarbon/$H_2S$ streams, the actual product yields will depend upon the hydrocarbon substrate and its concentration relative to that of $H_2S$ (or mercaptan). The rate of the process is limited by the partial pressure of $O_2$, the concentration of substrate, the concentration of catalyst [$Fe^{II}(DPAH)_2$], and temperature.

EXAMPLE IV

Activation of HOOH and t-BuOOH by $Co^{II}(bpy)_2^{2+}$ for the Oxygenation of Hydrocarbons, the Oxidation of Alcohols and Aldehydes and the Dioxygenation of Arylolefins and Acteylenes For activation of HOOH and t-BuOOH and conversion of various substrates, the substrates (1M) and $Co^{II}(bpy)_2^{2+}$ (20 mM) were combined in 7 mL of acetonitrile/pyridine (4:1 molar ratio) or 7 mL of acetonitrile, followed by the slow addition over a period of one to two minutes of either 100 µL of 17.6M HOOH (50% in $H_2O$) to give 200 mM HOOH, or 600 µL of 3.0 M t-BuOOH (in 2,2,4-trimethyl-pentane) to give 200 mM t-BuOOH. After six hours stirring at a temperature of 22°+ or −2° C., the reaction mixtures were analyzed by capillary gas chromatography and GC-MS, either by direct injection of the product solution, or by quenching with water and extracting with diethyl ether. The product concentrations obtained for a given concentration of substrate and oxident (either HOOH or t-BuOOH) are summarized in Table V.

TABLE V

Activation of HOOH and t-BuOOH by $Co^{II}(bpy)_2^{2+}$ for the Oxygenation of Hydrocarbons, the Oxidation of Alcohols and Aldehydes, and the Dioxygenation of Aryloefins and Acetylenes in 4:1 MeCN/py.

| substrate (1M) | oxidant (0.2M) | products (mM) |
| --- | --- | --- |
| c-$C_6H_{12}$ | HOOH | c-$C_6H_{10}(O)$ (61), c-$C_6H_{11}OH(1)$ |
| c-$C_6H_{12}$(MeCN) | HOOH | c-$C_6H_{10}(O)$ (14), c-$C_6H_{11}OH(9)$ |
| c-$C_6H_{12}$ | t-BuOOH | c-$C_6H_{11}OOBu$-t(1.5) |
| c-$C_6H_{12}$(MeCN) | t-BuOOH | c-$C_6H_{10}(O)$ (15),c-$C_6H_{11}OOBu$-t(2),c-$C_6H_{11}OH(1)$ |
| $Me_2CHCH_2Me$ | HOOH | $Me_2CHC(O)Me$(12),$Me_2C(OH)CH_2Me$(5) |
| $Me_2CHCH_2Me$ (MeCN) | t-BuOOH | $Me_2C(OH)CH_2Me$(9),$Me_2CHC(O)Me$(1) |
| $PhCH_2CH_3$ | HOOH | $PhC(O)Me$(30),$PhCH_2CH_2OH$(11) |
| $PhCH_3$ | HOOH | $PhCH(O)$ (20),$PhCH_2OH$(17) |
| $PhCH_3$(MeCN) | t-BuOOH | $PhCH_2OOBu$-t(28),$PhCH(O)$ (12) |
| c-$C_6H_{10}$ | HOOH | c-$C_6H_8$-2-ene-1-one(50),epoxide(8),c-$C_6H_8$-2-ene-1-ol(3) |
| c-$C_6H_{10}$(MeCN) | HOOH | R-OH(31),R-one(30),epoxide(12),R-R(1) |
| c-$C_6H_{10}$(MeCN) | t-BuOOH | R-OOBu-t(41),R-one(6),R-OH(3),R-R(1) |
| PhH(MeCN) | HOOH | PhOH(34) |
| c-$C_6H_{11}OH$(MeCN) | HOOH | c-$C_6H_{10}(O)$ (28) |
| $PhCH_2OH$(MeCN) | HOOH | $PhCH(O)$ (40) |
| $PhCH(O)$ (MeCN) | HOOH | $PhC(O)OH$(108) |
| c-PhCH=CHPh(0.65M) | HOOH | $PhCH(O)$ (87),epoxide(4) |
| PhC≡CPh | HOOH | $PhC(O)C(O)Ph$(24) |
| 2,6-$(Me)_2PhOH$ | HOOH | 2,6-$(Me)_2$-$p$-benzoquinone(5),ROOR(3) |
| 2,6-$(Me)_2PhOH$(MeCN) | t-BuOOH | ROOR(9) |

EXAMPLE V

Characterization of Catalysts

The results of Table IA indicate that in the presence of excess HOOH, $Fe(PA)_2$ and $(PA)_2FeOFe(PA)_2$(1)- [and Fe(DPA) and (DPA)FeOFe(DPA)(5)] were equally effective. However, when the concentrations of catalyst and HOOH were the same, the efficiency of $Fe(PA)_2$ for the oxygenation of cis-PhCH=CHPh was significantly less than with $(PA)_2FeOFe(PA)_2$ (Table IIIB). Addition of reduced amounts of HOOH (19 mM) to 19 mM $Fe(PA)_2$ or 19 mM $(PA)_2FeOFe(PA)_2$ and 1 M c-$C_6H_{12}$ in pyridine/HOAc resulted in major amounts of products [c-$C_6H_{11}$-py and (c-$C_6H_{11})_2$] from the production of c-$C_6H_{11}$ radicals via Fenton chemistry (Table IIIC). When $Fe(PA)_2$ was added to c-$C_6H_{12}$/HOOH, the reaction efficiency was enhanced as was the yield of c-$C_6H_{10}(O)$. The apparent second-order rate constant for the 1:1 combination of $Fe(PA)_2$/HOOH in py/HOAc was $(2\pm1)\times 10^3 M^{-1}s^{-1}$, but decreased to $(2\pm1)\times10^2 M^{-1}s^{-1}$ when the Fe(PA)$_2$/HOOH ratio was 1:200.

Spectrophotometric and cyclic voltammetric analysis indicated that in the absence of substrate, the combination of excess HOOH with two Fe(PA)$_2$ molecules ($\lambda_{max}$, 402nm) in the pyridine/HOAc solvent yielded (PA)$_2$FeOFe(PA)$_2$(1)(irreversible reduction at $-0.1$ V vs SCE and UV-visible absorption at $<400$nm) and (PA)$_2$Fe(OAc) (reversible cyclic voltammogram at $+0.2$ V vs SCE) in 2:1 pyridine/HOAc. As Table IA indicates, the use of the (PA)$_2$FeOFe(PA)$_2$(1) gave results that were equivalent to those of Fe(PA)$_2$, and prompts the conclusion that the latter is transformed in situ to 1.

In the contrast to the py/HOAc solvent, addition of HOOH to a solution of species 1 in Me$_2$SO rapidly evolved dioxygen (1 is insoluble in MeCN). The [2,6-dicarboxylato-pyridine]iron(II) complex, Fe(DPA), appeared to be a slightly superior catalyst to Fe(PA)$_2$, and paralleled the latter's transformation by HOOH to give the most active and selective catalyst, (DPA)-FeOFe(DPA)(5).

In dimethylformamide, the combination of two Fe(PA)$_2$ molecules with one HOOH resulted in the stoichiometric formation of [(PA)$_2$Fe(OH)]$_2$(1a); the apparent second-order rate constant was $2.5\times10^3 M^{-1}s^{-1}$. The same process occurred in pyridine/acetic acid, at approximately the same rate (k, $\sim1\times10^3 M^{-1}s^{-1}$). Likewise, Fe(DPA) was transformed by HOOH to [(DPA)Fe(OH)]$_2$; the rate of reaction is about an order of magnitude faster than for Fe(PA)$_2$ as determined by spectrophotometry and cyclic voltammetry.

When excess HOOH was added to [(PA)$_2$Fe(OH)]$_2$ (1a) or [(DPA)$_2$Fe(OH)]$_2$ in DMF, it decomposed rapidly to dioxygen and water. In contrast, the same experiment in pyridine/acetic acid did not result in the rapid decomposition of HOOH, again.

A. Production of Singlet Dioxygen ($^1O_2$)

Table VI summarizes the yields of singlet dioxygen from the addition of [(PA)$_2$Fe(OH)]$_2$ (1a) (in equilibrium with (PA)$_2$FeOFe(PA)$_2$(1b) shown in equation (2) below) to HOOH in dimethylformamide (DMF). The reaction of hydrogen peroxide with hypochlorus acid in deuterium oxide solvent was used as a $^1O_2$ standard ($^1O_2$ lifetimes: 62 $\mu$s for deuterium oxide and 17 $\mu$s for DMF). $^1O_2$ spectral analysis of near-infrared emission; filter, nm (Signal): 1170 (0.01), 1268 (1.00), 1375 (0.59) and 1470 (0.11). The concentration of $^1O_2$ generated was corrected for quenching by [(PA)$_2$Fe(OH)]$_2$ (k$_{q,a}$, $6.0\times10^9$ M$^{-1}$s$^{-1}$), where the total quenching at any reaction time is given by k$_{q,a}$ [[(PA)$_2$Fe(OH)]$_2$]+k$_{q,b}$ [(PA)$_2$FeOFe(PA)$_2$]. The rate constants were evaluated in DMF via photochemical generation of $^1O_2$ with rose bengal [bis(triethylammonium salt)]. Because the apparent quenching constant for [(PA)$_2$Fe(OH)]$_2$ decreased for concentrations above 250 $\mu$M, this correction method may overestimate the yield of $^1O_2$ at the high concentrations indicated by as much as 20%.

Both [(PA)$_2$Fe(OH)]$_2$ and its $\mu$-oxo-form, (PA)$_2$FeOFe(PA)$_2$(1b), quenched $^1O_2$ with apparent second-order rate constants of $6.0\times10^7 M^{-1}s^{-1}$ and $2.0\times10^9 M^{-1}s^{-1}$, respectively. Because essentially stoichiometric yields of singlet dioxygen resulted (one $^1O_2$ per 1a at high HOOH concentrations), the transition-state complex most likely involves a dioxygen adduct from the combination of two HOOH molecules with 1a. In contrast, control experiments with Fe(MeCN)$_4$(ClO$_4$)$_2$ resulted in the stoichiometric decomposition of HOOH to $^3O_2$ and H$_2$O, but there was no detectable production of $^1O_2$.

TABLE VI

Yields of Singlet Dioxygen ($^1O_2$) from the Combination of [(PA)$_2$Fe(OH)]$_2$ (1a) with Hydrogen Peroxide in Dimethylformamide.

| [(PA)$_2$Fe(OH)]$_2$ (1a), $\mu$M (corrected) | HOOH, mM | $^1O_2$, $\mu$M (uncorrected) | $^1O_2$, $\mu$M |
|---|---|---|---|
| 20 | 50 | 20 | 24 |
| 50 | 28 | 45 | |
| 100 | 50 | 32 | 69 |
| 250 | 50 | 37 | 153 |
| 500 | 50 | 46 | 273 |
| 1000 | 50 | 53 | 544 |
| 2000 | 50 | 53 $\pm$ 2$^a$ | 1013 $\pm$ 34$^a$ |
| 2000 | 100 | 103 | 1950 |
| 2000 | 25 | 24 | 457 |

$^a$Mean value $\pm$ standard error for 3 measurements.
Other values are for singles measurements.

B. Dioxygenation by [(Ph$_3$PO)$_4$FeOOFe(OPPh$_3$)$_4$](ClO$_4$)$_4$(4)

In pyridine/HOAc (mol-ratio, 2:1), a binuclear iron $\mu$-dioxygen complex (4) reacted with excess PhC≡CPh to give PhC(O)C(O)Ph exclusively (3% efficient in 15 min.; 0.6 M PhC≡CPh and 56 mM 4); and with excess cyclohexane to give cyclohexanone exclusively (3% efficient in 15 min.; 1M c-C$_6$H$_{12}$ and 56 mM 4). In MeCN, neither substrate reacted with 4; however, the addition of sufficient HClO$_4$ to make the solution 3.7 M caused PhC≡CPh to be transformed almost completely (one PhC≡CPh per 4) within 10 min. [yield 78% of PhC(O)C(O)Ph and 14% PhC(O)OH].

SUMMARY AND DISCUSSION OF THE EXAMPLES

The results of Table I establish that the pyridine/HOAc (mol-ratio, 2:1) solvent system is optimal for the efficient and selective ketonization of methylenic carbons by the Fe(PA)$_2$/HOOH system. On the basis of the relative reaction efficiencies for Fe(PA)$_2$ and (PA)$_2$FeOFe(PA)$_2$ (Tables IA and III), the initial step when Fe(PA)$_2$ is used as the catalyst is its transformation to (PA)$_2$FeOFe(PA)$_2$ (1). The spectrophotometric, electrochemical, and magnetic results for the combination of Fe(PA)$_2$ and HOOH in DMF confirm a 2:1 reaction stoichiometry to give a binuclear product (k$_1$, $2\times10^3 M^{-1}s^{-1}$)

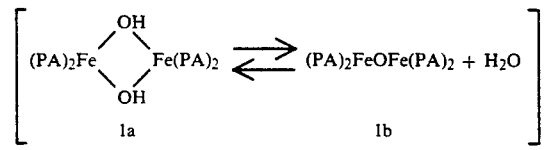

Electrochemical measurements established that (a) autoxidation of Fe(PA)$_2$ in MeCN yields a product that is a mixture of 1a and 1b, and (b) the product from the 1:1 combination of Fe(PA)$_3$ and $^-$OH in DMF is mainly 1b $$2Fe(PA)_3 + 2^-OH \longrightarrow \underset{1b}{(PA)_2FeOFe(PA)_2} + 2PA^- + H_2O \quad (3)$$

The addition of species 1a to excess HOOH in DMF results in near stoichiometric production of $^1O_2$ (Table IV) and yields species 1b during catalytic turnover:

$$1b + HOOH \longrightarrow \quad (4)$$

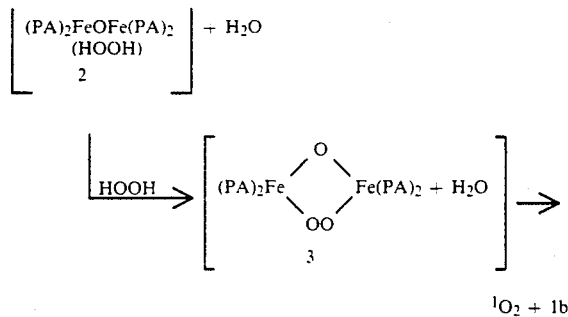

With low concentrations of HOOH as well as for reaction conditions with 1:1 Fe(PA)$_2$/HOOH, the Fenton process becomes dominant (Table IIIC)(14).

$$Fe(PA)_2 + HOOH \rightarrow (PA)_2Fe(OH) + \cdot OH \quad (5a)$$

$$\cdot OH + RH \rightarrow R \cdot (or \tfrac{1}{2}R_2) + H_2O \quad (5b)$$

$$\cdot OH + py \rightarrow py\cdot [or\ 1/n(pyOH)_n] + H_2O \quad (5c)$$

For the conditions of the experiments that are summarized in Tables I and II (excess HOOH added to catalyst/substrate), the reaction sequence of eq. 2 and eq. 4 prevails to a major degree [with no evidence of Fenton chemistry (eq. 5) in the product profiles]. The results of Table II indicate that the relative reactivity of species 3 with hydrocarbon substrates in the order $CH_2 > PhC \equiv CPh > >ArCH = CHR- > >Ar-CH_3 > >CH$, which is completely at odds with radical processes (19).

Referring to Scheme I below, the data of Tables I–III, together with what is known in the literature about the [Fe(MeCN)$_4$](ClO$_4$)$_2$/2HOOH system (7,20), prompt the formulation of reaction steps and pathways for the (PA)$_2$FeOFe(PA)$_2$/HOOH/(py/HOAc)/substrate system as shown in Scheme Ia. On the basis of the product profiles and reaction efficiencies (Tables I–III) when (PA)$_2$FeOFe(PA)$_2$ (or its precursor, Fe(PA)$_2$, eq. 2) is used as the catalyst, the initial step in the catalytic reaction cycle appears to be the formation of an HOOH adduct [(PA)$_2$FeOFe(PA)$_2$(HOOH)](2). In the presence of >CH$_2$ or RC≡CR groups, species 2 rapidly forms (with another HOOH) the activated complex (species 3, Scheme Ia). The pre-catalyst (species 2) reacts with selective substrates in a manner that is analogous to that of other iron-HOOH adducts. Previous studies have demonstrated that similar iron-oxene species are formed from the 1:1 combination of HOOH and [Fe(MeCN)$_4$](ClO$_4$)$_2$, (5, 11), [(Ph$_3$PO)$_4$Fe](ClO$_4$)$_2$ (9), and FeCl$_3$ (21). Thus, for conditions that favor formation of species 2 (i.e., 1:1 (PA)$_2$FeOFe(PA)$_2$/HOOH, Table IIIB) epoxidation of c-PhCH=CHPh is enhanced, but for conditions that favor species 3 (i.e., 20:1 (PA)$_2$FeOFe(PA)$_2$/HOOH) dioxygenation is the dominant path (Table II).

Scheme Ia.

(a) Reaction Paths

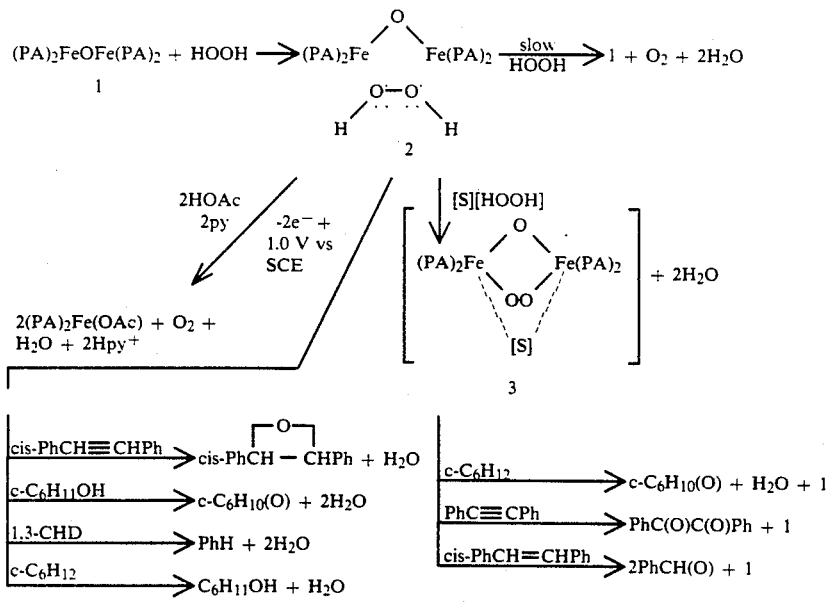

Scheme Ib.

(b) Proposed Mechanisms

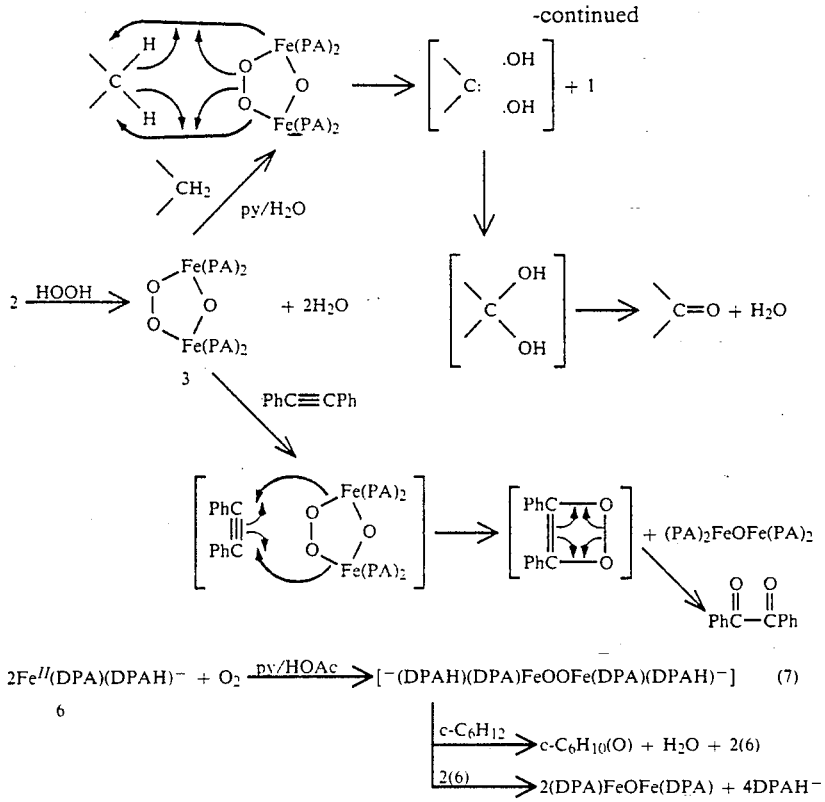

$$2Fe^{II}(DPA)(DPAH)^- + O_2 \xrightarrow{py/HOAc} [^-(DPAH)(DPA)FeOOFe(DPA)(DPAH)^-] \quad (7)$$

$$\begin{array}{l} \xrightarrow{c-C_6H_{12}} c-C_6H_{10}(O) + H_2O + 2(6) \\ \xrightarrow{2(6)} 2(DPA)FeOFe(DPA) + 4DPAH^- \end{array}$$

Species 3 transforms methylenic carbons ($CH_2$) to carbonyls (C=O) and dioxygenates acetylenes and arylolefins, which parallels the reactivity of [($Ph_3PO)_4$-FeOOFe($OPPh_3)_4$]($ClO_4)_4$(4)(12)

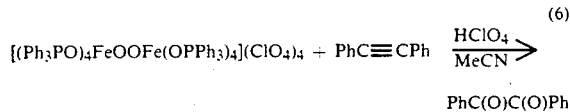

PhC(O)C(O)Ph and of the apparent intermediate from the combination of $Fe^{II}$(DPA)(DPAH)$^-$ and $O_2$. The catalytic cycles for Fe(DPA) and (DPA)FeOFe(DPA) ($), which are the most effective and selective catalysts of the iron complexes investigated (Table IA), appear to be analogous to those for Fe(PA)$_2$ and (PA)$_2$FeOFe(PA)$_2$(1)(eq. 2 and 4, and Scheme Ia).

Scheme Ib outlines a proposed concerted, singlet-biradical mechanism for the selective ketonization of methylenic carbons and dioxygenation of acetylenes via a common reactive intermediate, species 3, which evolves $^1O_2$ in substrate-free DMF (Table V). The ketonization of a methylene group in cyclohexene and 1,4-cyclohexadiene (Table III) is especially compelling evidence for a concerted selective process that is optimal for the geometry of methylenic carbons. In contrast, the dehydrogenation of 1,3-cyclohexadiene (Table II) probably is the result of selective reactivity with the pre-catalyst, species 2 (Scheme Ia).

Referring now to Table IV, the products resulting from the activation of dioxygen are identical to those that result from the reactive intermediate from the combination of (DPA)FeOFe(DPA) and excess HOOH, which is believed to be (DPA)FeOOFe(DPA). The dioxygenation of the substrates in Table IV is thought to result from a similar reactive intermediate [but $Fe^{II}$(DPAH)$_2$ is one and one-half times as efficient as $Fe^{II}$(DPA)]. With cyclohexane about one-fourth of the $O_2$ that is incorporated into the reactive intermediate reacts to give cyclohexanone as the only detectable product; the remainder oxidizes the excess $Fe^{II}$(DPAH)$_2$ to give (DPAH)$_2$FeOFe(DPAH)$_2$, which is catalytically inert.

If the combination of $Fe^{II}$(DPA)$_2$ and $O_2$ results in the initial formation of the reactive intermediate [(DPAH)$_2$FeOOFe(DPAH)$_2$] via a rate-limiting step

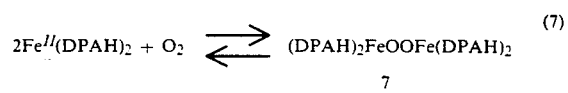

(7)

then, the results of Table IV indicate that K is less than unity. Thus, the yield of cyclohexanone increases linearly with $Fe^{II}$(DPAH)$_2$ concentration. The apparent rate for the ketonization reaction is proportional to substrate concentration, $Fe^{II}$(DPAH)$_2$ concentration, and $O_2$ partial pressure, and increases with temperature (about five times faster at 25 C than at 0 C). Because the fraction of (7) that reacts with c-$C_6H_{12}$ remains constant ($\sim$28%), the oxidation of excess $Fe^{II}$(DPAH)$_2$ by (7) must be a parallel process. Given that the ratio of concentrations [c-$C_6H_{12}$/$Fe^{II}$(DPAH)$_2$] is about 30:1 and the ratio of reactivities is 1:2.6, then the apparent relative rate constant for reaction of c-$C_6H_{12}$ and $Fe^{II}$(DPAH)$_2$ with (7) is about 0.02 $k_{FeII}$ (assuming a stoichiometric factor of 2 for the latter).

The results of Table IV and the close parallels of the product profiles to those for the (pA)$_2$FeOFe(PA)$_2$-/HOOH/(by/HOAc) system prompt the conclusion that the reactive intermediate for the $Fe^{II}$(DPAH)$_2$/$O_2$ combination is $(DPAH)_2FeOOFe(DPAH)_2$ (7, eq. 7), and are the basis for the reaction pathways outlined in Scheme II.

When t-BuOOH is the oxygen source the reactivity with substrates is about ten times greater in pure MeCN than in MeCN/py (Table V). With $PhCH_3$, the domi-

Scheme II.
Activation of $O_2$ by $Fe_{II}(DPAH)_2$ in $py_2$/HOAc

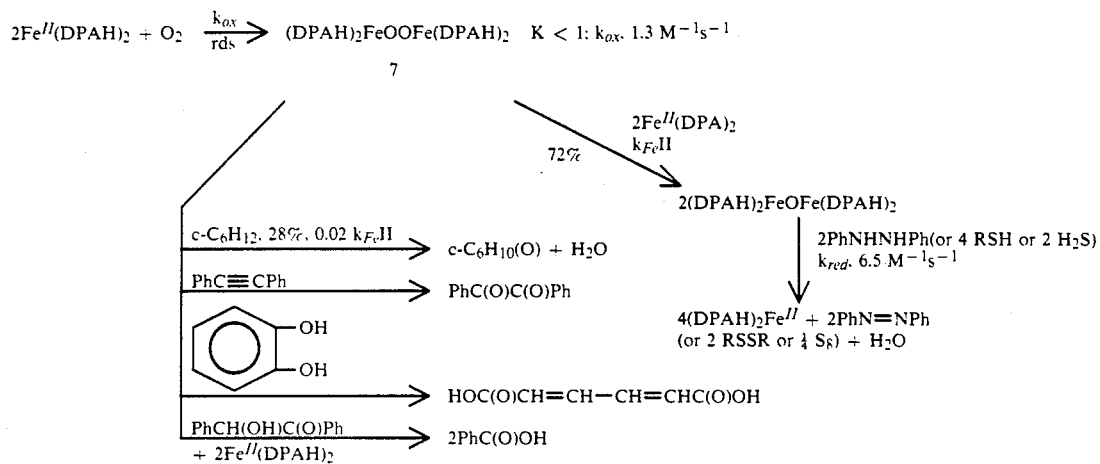

Table V summarizes the product distributions for a series of substrates that result from the catalytic activation of HOOH or t-BuOOH by $Co^{II}(bpy)_2^{2+}$. The product profiles indicate the oxidase (or monooxygenase) chemistry is favored in pure MeCN solvent (c-$C_6H_{12}\rightarrow$c-$C_6H_{11}OH$), but the ketonization of methylenic carbon and dioxygenase chemistry are favored in MeCN/py(4:1 molar ratio) [c-$C_6H_{12}\rightarrow$c-$C_6H_{10}(O)$; c-PhCH=CHPh$\rightarrow$2PhCH(O)]. The selective ketonization of cyclohexene in MeCN/py contrasts with its enhanced monooxygenation in pure MeCN (one/ol ratio; 16:1 vs. 1:1), and is compelling evidence for two reactive intermediates. The presence of $O_2$ inhibits the reactivity of c-$C_6H_{12}$ with HOOH by 10-20%. In pure MeCN $Co^{II}(bpy)^{2+}$ catalyzes HOOH for the stoichiometric transformation of 1,4-cyclohexadiene to benzene.

nant product is $PhCH_2OOBu$-t, which requires two t-BuOOH molecules per substrate. When c-$C_6H_{12}$ is the substrate, c-$C_6H_{10}(O)$ and c-$C_6H_{11}OOBu$-t are the major products (both require two t-BuOOH molecules per substrate) and the ketone probably results from the decomposition of c-$C_6H_{11}OOBu$-t. In contrast, with $(Me)_2CHCH_2Me$ the major product is $(Me)_2$-$C(OH)CH_2Me$ (one t-BuOOH per substrate). The use of t-BuOOH precludes (or strongly suppresses) formation of the reactive intermediate for the direct ketonization of methylenic carbons.

The results of Table V and the close parallels of the product profiles to those for the $Fe^{II}(PA)_2/HOOH$/-(py/HOAc) system prompt the conclusion that the combination of $Co^{II}(bpy)^{2+}$(1) and HOOH results in the initial formation of an oxene intermediate [(bpy)$^{2-}$+$Co^{II}O$,2], which (in MeCN/py) rapidly reacts with a second HOOH to give a dioxygenase reactive intermediate [(bpy)$^{2+}CO^{II}OOCo^{III}$(bpy)$^{2+}$,3] (Scheme III).

Scheme III.
Activation of HOOH and t-BuOOH by $Co^{II}(bpy)_2^{2+}$.

a. HOOH(MeCN/py); [MeCN]

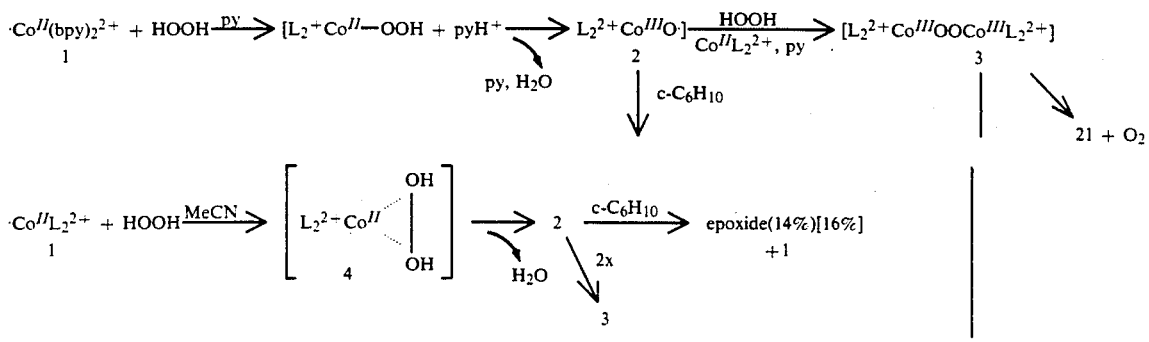

-continued
Scheme III.
Activation of HOOH and t-BuOOH by $Co^{II}(bpy)_2^{2+}$.

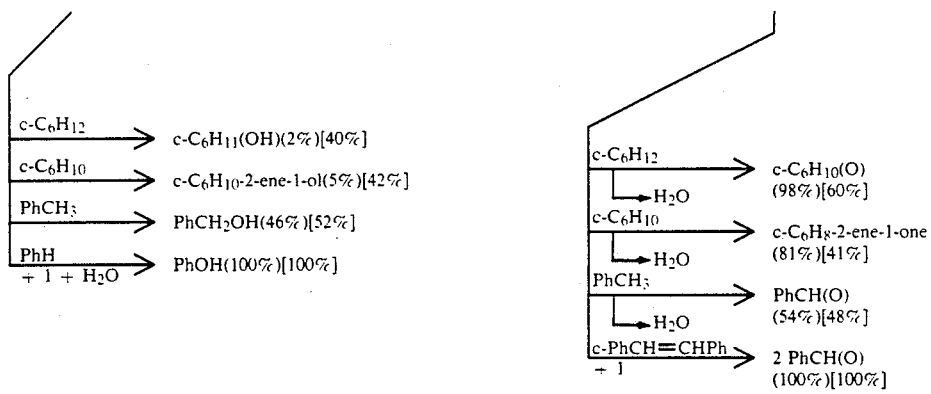

b. t-BuOOH [MeCN]

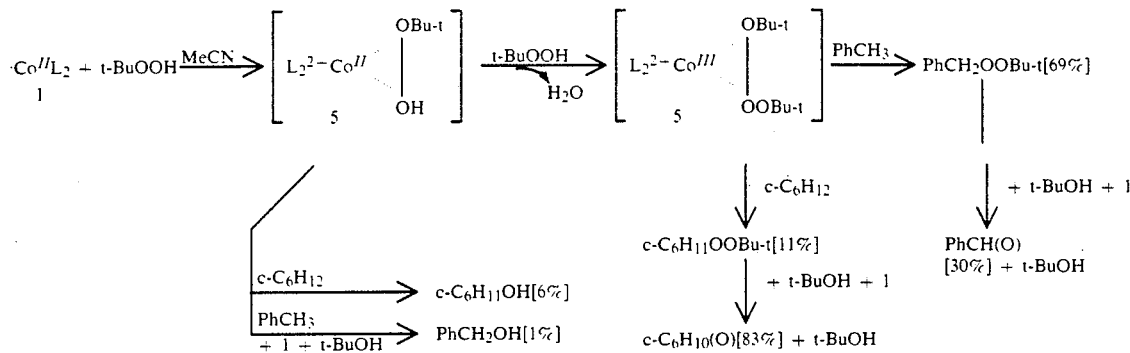

In pure MeCN, species 1 appears to activate HOOH and t-BuOOH via formation of 1:1 adducts [(bpy)$_2$+Co$^{II}$(HOOH),4 and (bpy)$_2$+Co$^{II}$(t-BuOOH),5], which, when formed in the presence of substrates, act as monooxygenases (c-C$_6$H$_{12}$→c-C$_6$H$_{11}$OH).

As such, they are closely similar to the reactive intermediate from the combination of [Fe$^{II}$(MeCN)$_4$](ClO$_4$)$_2$ and HOOH in MeCN. The formation of two reactive intermediates [4, favored in MeCN and 3, favored in MeCN/py] in combination with the product profiles of Table V is the basis for the proposed reaction pathways of Scheme III. Species 3 transforms methylenic carbons (>CH$_2$) to ketones (>C=O) and dioxygenates arylolefins and acetylenes, and its precursor (species 2) epoxidizes aliphatic olefins. Combination of t-BuOOH and Co$^{II}$(bpy)$_2$ appears to form intermediates 5 and 6; species $ has similar reactivity to species 4, but species 6 is unique and necessary to account for the observed ROOBu-t products.

In summary, the Co$^{II}$(bpy)$^{2+}$/HOOH/(4:1 MeCN/py) system forms a reactive intermediate (3) that selectively ketonizes methylenic carbon, and as such is closely similar to the intermediate of the Fe$^{II}$(PA)$_2$/HOOH/(2:1 py/HOAc) system and of related systems. We believe that the common feature is a stabilized-dioxygen intermediate rather than a hypervalent metal-centered carbon oxidant. The ability of Fe$^{II}$(DPAH)$_2$ to activate O$_2$ to an intermediate that has the same unique selectivity for hydrocarbon ketonization is further support for a common stabilized-dioxygen reactive complex. Several cobalt/dioxygen complexes exhibit oxygenase reactivity with organic substrates, which is consistent with the dioxygen formulation for species 3.

Other embodiments of the invention will be apparent to those skilled in the art from a consideration of the foregoing specification or practice of the invention disclosed herein.

LITERATURE CITED IN THE SPECIFICATION

1. Barton, D. H. R.; Gastiger, M. J.; Motherwell, W. B. J., J. Chem. Soc., Chem. Commun. 1983, 41.
2. Barton, D. H. R.; Boivin, J.; Motherwell, W. B.; Ozbalik N.; Schwartzentruber, K. M.; Jankowski, K., Nouv. J. Chim. 1986, 10, 387
3. Balavoine, G.; Barton, D. H. R.; Boivin, J.; Gref, A.; Ozbalik, N.; Riviére, H., J. Chem. Soc., Chem. Commun. 1986, 1727.
4. Balavoine, G.; Barton, D. H. R.; Boivin, J.; Gref, A.; Ozbalik, N.; Riviére, H. Tetrahedron Letts. 1986, 27, 2849.
5. Balavoine, G.; Barton, D. H. R.; Boivin, J.; Gref, A.; LeCoupanec, P.; Ozbalik, N.; Pestana, A.; Riviére, H. Tetrahedron 1988, 44, 1091.
6. Barton, D. H. R.; Boivin, J.; Ozbalik, N.; Schwartzentruber, K. M; Jankowski, K. Tetrahedron Letts. 1985, 26, 447.
7. Sugimoto, H.; Sawyer, D. T. J. Am. Chem. Soc. 1984, 106, 4283.
8. Walling, C. Acc. Chem. Res. 1975, 8, 125.
9. Kanofsky, J. R. J. Biol. Chem. 1983, 258, 5991.
10. Kanofsky, J. R. J. Biol. Chem. 1988, 263, 14171.
11. Evans, D. F. J. Chem. Soc. 1959, 2003.

12. Sawyer, D. T.; McDowell, M. S.; Spencer, L.; Tsang, P. K. S. *Inorg. Chem.* 1989, 28, 1166.
13. Sawyer, D. T.; Calderwood, T. S.; Yamaguchi, K.; Angelis, C. T. *Inorg. Chem.* 1982, 22, 2577.
14. Yamaguchi, K.; Calderwood, T. S.; Sawyer, D. T. *Inorg. Chem.* 1986, 25, 1289.
15. Karayannis, N. M.; Mikulski, C. M.; Strocko, M. J.; Pytlewski, L. L.; Labes, M. M. *J. Inorg. Nucl. Chem.* 1970, 32, 2629.
16. Calderwood, T. S.; Johlman, C. L.; Roberts, J. L., Jr.; Wilkins, C. L.; Sawyer, D. T. *J. Am. Chem. Soc.* 984, 106, 4683.
17. (a) Hayaishi, O.; Nozaki, M.; Abbott, M. T. In "The Enzymers," Boyer, P. D., Ed.; Academic Press: New York, 1975, Vol. XII, pp. 119, 189. (b) Que, L.; Jr. *Adv. Inorg. Biochem.* 1983, 5, 167.
18. (a) Que, L., Jr., *J. Chem. Ed.* 1985, 62, 938. (b) Weller, M. G.; Weser, U. *J. Am. Chem. Soc.* 1982, 104, 3752. 19. Sheu, C.; Sobkowiak, A.; Zhang, L.; Ozbalik, N.; Barton, D. H. R.; Sawyer, D. T. *J. Am. Chem. Soc.* 1989, 111, 8030.
20. Sugimoto, H.; Sawyer, D. T. *J. Am. Chem. Soc.* 1985, 107, 5712.
21. Sugimoto, H.; Sawyer, D. T. *J. Inorg. Chem.* 1985, 50, 1784.

We claim:

1. A process for the oxygenation of an organic compound which comprises contacting said organic compound with a complex of formula $(L)_lM(OM)_m(L')_n(A)_p$ in which L and L' are the same or different and each is a ligand of formula

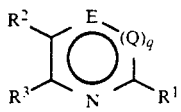

wherein:
$R^1$ is hydrogen, $CO_2^-$ or $CO_2H$;
$R^2$ is hydrogen or alkyl;
$R^3$ is hydrogen, $CO_2^-$, $CO_2H$ or pyridinyl; or
$R^2$ and $R^3$ joined together and taken with the other atoms in the ring form a quinoline ring which is unsubstituted or substituted in the 8-position of $O^-$;
E is CH, N, NH or $CR^4$ wherein $R^4$ is alkyl;
Q is CH;
q is 0 or 1 provided that when q is 0, there is no Q substituent, E and the carbon atom to which $R^1$ is attached are joined directly and E is NH;
M is a transition metal cation;
O is oxygen;
A is an anion of an organic or mineral acid or is a halogen anion;
l is 1, 2, 3 or 4;
m is 0 or 1;
n is 0, 1, 2, 3 or 4; and
p is 0, 1 or 2; in the presence of dioxygen under conditions suitable for said conversion to take place, provided that M is in its reduced state and L is at least monosubstituted by $CO_2^-$ or $CO_2H$ when M is Fe, and L is not quinolinolate or quinolinol when M is Fe and L is not picolinolate or picolinic acid when M is Mn or Co.

2. A process as recited in claim 1, wherein a methylenic carbon contained in said organic compound is converted to a carbonyl.

3. A process as recited in claim 2, wherein said organic compound is a compound of formula I

wherein
$R^5$ and $R^6$ are the same or different and each is hydrogen, hydroxyl, alkyl or is aryl which is unsubstituted or mono- or polysubstituted by halogen, $NO_2$, OH, loweralkyl or loweralkoxy, or $R^5$ and $R^6$ taken together form a $C_3-C_{13}$ saturated or unsaturated ring, provided $R^5$ and $R^6$ are not both hydrogen and are not both hydroxyl, and is converted to a carbonyl compound of formula II

wherein
$R^5$ and $R^6$ are as defined above, wherein in said complex:
L and L' are the same or different and each is a ligand of formula

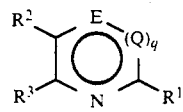

wherein:
$R^1$ is hydrogen, $CO_2^-$ or $CO_2H$;
$R^2$ is hydrogen or alkyl;
$R^3$ is hydrogen, $CO_2^-$, $CO_2H$ or pyridinyl;
E is CH, N, NH or $CR^4$ wherein $R^4$ is alkyl;
Q is CH;
q is 0 or 1 provided that when q is 0, there is not Q substituent, E and the carbon atom to which $R^1$ is attached are joined directly and E is NH;
M is a transition metal cation;
O is oxygen;
A is an anion of an organic or mineral acid or a halogen anion;
l is 1, 2, 3 or 4;
m is 0 or 1;
n is 0, 1, 2, 3 or 4; and
p is 0, 1 or 2; provided that $R^1$ and $R^3$ are the same or different and each is $CO_2^-$ or $CO_2H$ when M is Fe.

4. A process as claimed in claim 3, wherein $R^5$ and $R^6$ are the same or different and each is alkyl or aryl.

5. A process as recited in claim 4, wherein said compound of formula I is cyclohexane, ethylbenzene, 2-methyl-butane or cyclohexene and said complex is $Fe^{II}(DPAH)_2$.

6. A process as recited in claim 3, wherein said contact is made in the presence of dioxygen and a reductant.

* * * * *